(12) United States Patent
Chatani et al.

(10) Patent No.: US 12,297,301 B2
(45) Date of Patent: May 13, 2025

(54) HIGH-MOLECULAR-WEIGHT COMPOUND AND METHOD FOR PRODUCING SAME, COMPOSITION AND METHOD FOR PRODUCING SAME, RESIN COMPOSITION, ADDITIVE FOR LUBRICATING OIL, AND LUBRICATING OIL

(71) Applicant: Mitsubishi Chemical Corporation, Tokyo (JP)

(72) Inventors: Shunsuke Chatani, Tokyo (JP); Yuki Miyahara, Tokyo (JP); Hiroshi Niino, Tokyo (JP); Masashi Ikawa, Tokyo (JP); Haruki Okada, Tokyo (JP); Fumiko Fujie, Tokyo (JP)

(73) Assignee: Mitsubishi Chemical Corporation, Tokyo (JP)

( * ) Notice: Subject to any disclaimer, the term of this patent is extended or adjusted under 35 U.S.C. 154(b) by 93 days.

(21) Appl. No.: 17/460,140

(22) Filed: Aug. 27, 2021

(65) Prior Publication Data
US 2021/0403619 A1 Dec. 30, 2021

Related U.S. Application Data

(63) Continuation of application No. PCT/JP2020/014187, filed on Mar. 27, 2020.

(30) Foreign Application Priority Data

Mar. 29, 2019 (JP) ................ 2019-068999
Mar. 29, 2019 (JP) ................ 2019-069000
Mar. 29, 2019 (JP) ................ 2019-069001

(51) Int. Cl.
| | | |
|---|---|---|
| C08F 120/14 | (2006.01) | |
| C07C 321/14 | (2006.01) | |
| C07C 333/04 | (2006.01) | |
| C08L 33/12 | (2006.01) | |
| C10M 151/02 | (2006.01) | |
| C10M 151/04 | (2006.01) | |
| C10M 169/04 | (2006.01) | |
| C10N 30/00 | (2006.01) | |
| C10N 30/02 | (2006.01) | |

(52) U.S. Cl.
CPC .......... *C08F 120/14* (2013.01); *C07C 321/14* (2013.01); *C07C 333/04* (2013.01); *C08L 33/12* (2013.01); *C10M 151/02* (2013.01); *C10M 151/04* (2013.01); *C10M 169/041* (2013.01); *C08F 2810/20* (2013.01); *C10M 2203/003* (2013.01); *C10M 2221/02* (2013.01); *C10N 2030/02* (2013.01); *C10N 2030/68* (2020.05)

(58) Field of Classification Search
CPC ... C07C 321/14; C07C 333/04; C08F 120/14; C08F 2810/20; C08L 33/12; C10M 151/02; C10M 16/041; C10M 2203/003; C10M 2221/02; C10N 2030/02; C10N 2030/68
See application file for complete search history.

(56) References Cited

U.S. PATENT DOCUMENTS

| | | | |
|---|---|---|---|
| 4,061,864 A | 12/1977 | Guthrie et al. | |
| 5,679,762 A | 10/1997 | Yoshida et al. | |
| 9,290,462 B1 | 3/2016 | Luebben | |
| 10,144,900 B1 | 12/2018 | Kwak | |
| 2007/0244018 A1 | 10/2007 | Visger et al. | |
| 2010/0233595 A1* | 9/2010 | Takahashi | C08F 2/38 430/7 |

FOREIGN PATENT DOCUMENTS

| | | |
|---|---|---|
| CN | 101087823 A | 12/2007 |
| CN | 101260162 A | 9/2008 |
| JP | H07-179538 A | 7/1995 |
| JP | 2001064252 A * | 3/2001 |
| JP | 2007-277514 A | 10/2007 |
| JP | 2008-518052 A | 5/2008 |
| WO | 2006/047398 A2 | 5/2006 |

OTHER PUBLICATIONS

International Search Report issued in related International Patent Application No. PCT/JP2020/014187 dated Jun. 16, 2020.
Extended European Search Report issued in related European Patent Application No. 20783889.7 dated Jul. 14, 2022.
Office Action issued in related Japanese Patent Application No. 2021-512042 dated Apr. 5, 2022.
Partial Supplementary European Search Report issued in related European Patent Application No. 20783889.7 dated Apr. 21, 2022.
Office Action issued in related Chinese Patent Application No. 202080012796.6 dated Dec. 19, 2022.
Office Action issued in related Chinese Patent Application No. 202080012796.6 dated Aug. 9, 2023.

* cited by examiner

*Primary Examiner* — James C Goloboy
(74) *Attorney, Agent, or Firm* — Morgan, Lewis & Bockius LLP

(57) ABSTRACT

A high-molecular-weight compound having a plurality of polymer chains linked through a divalent or higher-valent linking group, in which the divalent or higher-valent linking group has a thiol group and at least one of a thioether structure and a thiourethane structure, and a ratio of an absolute weight-average molecular weight to a relative weight-average molecular weight (absolute Mw/relative Mw) of the high-molecular-weight compound is 1.25 or more; and a method for producing the same are provided.

19 Claims, No Drawings

HIGH-MOLECULAR-WEIGHT COMPOUND AND METHOD FOR PRODUCING SAME, COMPOSITION AND METHOD FOR PRODUCING SAME, RESIN COMPOSITION, ADDITIVE FOR LUBRICATING OIL, AND LUBRICATING OIL

This application is a continuation filing of, and claims priority under 35 U.S.C. § 111(a) to, International Application No. PCT/JP2020/014187, filed on Mar. 27, 2020, and claim priority under 35 U.S.C. § 119 to Japanese Patent Application Nos. 2019-68999, 2019-69000, and 2019-69001, filed on Mar. 29, 2019, the contents of which are incorporated herein by reference.

BACKGROUND OF THE INVENTION

Field of the Invention

The present invention relates to a high-molecular-weight compound and a method for producing the same, a composition and a method for producing the same, a resin composition, an additive for a lubricating oil, and a lubricating oil.

Description of the Related Art

High-molecular-weight compounds having a plurality of polymer chains bonded to a thiol group in a molecule thereof are used in paints, adhesives, pressure-sensitive adhesives, compatibilizers, dispersants, and the like.

JP 2001-064252 A (Patent Document 1) discloses a high-molecular-weight compound in which vinyl-based monomers are radically polymerized using an organic sulfide compound, obtained by subjecting a polyvalent mercaptan and a vinyl-based compound to a Michael-addition, as a chain transfer agent.

JP H07-179538 A (Patent Document 2) discloses a high-molecular-weight compound having a structure in which a plurality of polymer chains are radially extended around a polyvalent mercaptan moiety, and having a number-average molecular weight of 2,000 to 1,000,000, in which the plurality of polymer chains have two or more different compositions.

SUMMARY OF INVENTION

Technical Problem

A coating film using a thermoplastic resin generally has insufficient physical properties such as heat resistance. Thus, various additives are used to improve the physical properties. However, when a high-molecular-weight compound is used as the additive, there is a problem in that the viscosity of a paint increases and painting work becomes difficult.

Also, when the high-molecular-weight compounds described in Patent Documents 1 and 2 are added to a thermoplastic resin, it is difficult to achieve both of an effect of improving heat resistance and an effect of suppressing an increase in the viscosity of a solution.

An object of the present invention is to provide a high-molecular-weight compound which has an effect of improving the heat resistance of a thermoplastic resin and suppressing an increase in the viscosity of a solution to which the high-molecular-weight compound is added; and a method for producing the same.

Solution to Problem

The present invention has the following configurations.

<1> A high-molecular-weight compound comprising a plurality of polymer chains linked through a divalent or higher-valent linking group, wherein
   the divalent or higher-valent linking group has a thiol group and at least one of a thioether structure and a thiourethane structure, and
   a ratio of an absolute weight-average molecular weight to a relative weight-average molecular weight (absolute Mw/relative Mw) of the high-molecular-weight compound is 1.25 or more.

<2> The high-molecular-weight compound as described in <1>, wherein the divalent or higher-valent linking group includes at least one of structures represented by Formulae (1) and (2),

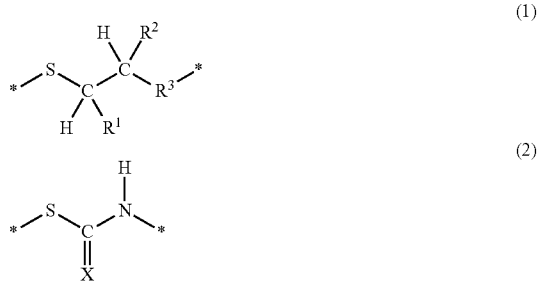

wherein, in Formula (1), $R^1$ and $R^2$ are each independently a hydrogen atom, a monovalent hydrocarbon group, a hydroxyl group, or a monovalent electron-withdrawing group, and $R^3$ is an oxygen atom, a divalent hydrocarbon group, or a divalent electron-withdrawing group, in Formula (2), X is an oxygen atom or a sulfur atom, and in Formulae (1) and (2), -* is a bond.

<3> The high-molecular-weight compound as described in <1>, wherein the divalent or higher-valent linking group has 1 to 300 thiol groups per molecule of the high-molecular-weight compound.

<4> The high-molecular-weight compound as described in <1>, wherein the absolute Mw/relative Mw is 3.00 or less.

<5> A method for producing a high-molecular-weight compound, comprising the steps of:
   reacting a polyfunctional thiol compound (A) with a compound (B) having a reactive group that reacts with a thiol group to obtain a chain transfer agent (F) having a thiol group; and
   polymerizing vinyl-based compounds in the presence of the chain transfer agent (F) having a thiol group and a radical polymerization initiator to obtain a high-molecular-weight compound.

<6> The method for producing a high-molecular-weight compound as described in <5>, wherein the reactive group that reacts with a thiol group is one or more selected from the group consisting of an acrylate group, a glycidyl group, and an isocyanate group.

<7> A composition comprising a compound (E) having a moiety derived from a polyfunctional thiol compound (A) and a moiety derived from a compound (B) having a reactive group that reacts with a thiol group, as a main component,
   wherein the composition satisfies Formulae (11) and (12), $$r \times (f_A - 1) \times (f_B - 1) < 1.2 \qquad (11)$$

$$r = (f_B \times y)/(f_A \times x) \qquad (12)$$

wherein, in Formula (11), $f_A$ is an average number of thiol groups per molecule of the polyfunctional thiol compound (A), $f_B$ is an average number of reactive groups per molecule of the compound (B), $f_A$ is 2.0 or more and $f_B$ is 1.2 or more, provided that a case where only the compound (A) having two thiol groups and only the compound (B) having two reactive groups are used is excluded, and r is a value calculated by Formula (12) when a molar ratio of the moiety derived from the polyfunctional thiol compound (A) to the moiety derived from the compound (B) is defined as x:y.

<8> The composition as described in <7>, wherein the compound (E) is a compound having at least one thiol group per molecule.

<9> The composition as described in <7>, wherein the composition satisfies $f_A+f_B>4.0$.

<10> The composition as described in <7>, wherein the reactive group that reacts with a thiol group is one or more selected from the group consisting of an acrylate group, a glycidyl group, and an isocyanate group.

<11> The composition as described in <7>, wherein the composition is a chain transfer agent in a radical polymerization reaction system.

<12> A method for producing a composition, comprising the step of:

reacting a polyfunctional thiol compound (A) and a compound (B) having a reactive group that reacts with a thiol group under conditions satisfying Formulae (13) and (14), $$r' \times (f_A-1) \times (f_B-1) < 1.2 \quad (13)$$

$$r' = (f_B \times y')/(f_A \times x') \quad (14)$$

wherein, in Formula (13), $f_A$ is an average number of thiol groups per molecule of the polyfunctional thiol compound (A), $f_B$ is an average number of reactive groups per molecule of the compound (B), $f_A$ is 2.0 or more and $f_B$ is 1.2 or more, provided that a case where only the compound (A) having two thiol groups and only the compound (B) having two reactive groups are used is excluded, and r' is a value calculated by Formula (14) when a molar ratio of the polyfunctional thiol compound (A) to the compound (B) is x':y'.

<13> The method for producing a composition as described in <12>, wherein the composition satisfies $f_A+f_B>4.0$.

<14> The method for producing a composition as described in <12>, wherein the polyfunctional thiol compound (A) is reacted with the compound (B) having a reactive group that reacts with a thiol group in the presence of a catalyst (C).

<15> The method for producing a composition as described in <12>, wherein the amount of solvent at a starting time of the reaction between the polyfunctional thiol compound (A) and the compound (B) having a reactive group that reacts with a thiol group is 50% by mass or less of a total mass of the polyfunctional thiol compound (A) and the compound (B) having a reactive group that reacts with a thiol group, and an external temperature during the reaction between the polyfunctional thiol compound (A) and the compound (B) having a reactive group that reacts with a thiol group is 10° C. to 50° C.

<16> A resin composition comprising:
the high-molecular-weight compound as described in <1>; and
a thermoplastic resin.

<17> The resin composition as described in <16>, wherein a mass ratio of the high-molecular-weight compound or the composition to the thermoplastic resin ((high-molecular-weight compound or composition)/thermoplastic resin) is 0.1/99.9 to 95/5.

<18> An additive for a lubricating oil, comprising the high-molecular-weight compound as described in <1>.

<19> The additive for a lubricating oil as described in <18>, wherein a relative Mw of the high-molecular-weight compound is 15,000 to 45,000.

<20> A lubricating oil comprising the additive for a lubricating oil as described in <18>.

Advantageous Effects of Invention

According to the present invention, it is possible to provide a high-molecular-weight compound which has an effect of improving the heat resistance of a thermoplastic resin and suppressing an increase in the viscosity of a solution to which the high-molecular-weight compound is added; and a method for producing the same.

In addition, according to the present invention, it is possible to provide a composition having excellent solubility in a polymerization solvent or a monomer, and a method for producing the same. The present composition can be suitably used for production of the high-molecular-weight compound as a chain transfer agent. In addition, the present composition has an effect of improving the heat resistance of a thermoplastic resin and suppressing an increase in the viscosity of a solution to which the composition is added.

Furthermore, according to the present invention, it is possible to provide a resin composition having excellent heat resistance and excellent handleability in painting work and the like. The present resin composition can also suppress adverse effects such as foaming due to volatilization of thermally decomposed components.

Moreover, according to the present invention, in a lubricating oil, it is possible to provide an additive for a lubricating oil, which imparts a viscosity index sufficiently satisfying required performance even when a temperature fluctuates, and has high shear stability. A lubricating oil including the additive has a small change in the viscosity due to temperature fluctuation and has high shear stability.

DETAILED DESCRIPTION OF THE INVENTION

In the present specification and claims, a numerical range represented by "-" means a numerical range including each of the numerical values before and after—as a lower limit value and an upper limit value.

[High-Molecular-Weight Compound and Method for Producing Same]

The high-molecular-weight compound of the present invention is a high-molecular-weight compound having a plurality of polymer chains linked through a divalent or higher-valent linking group, in which the divalent or higher-valent linking group has a thiol group and at least one of a thioether structure and a thiourethane structure, and a ratio of an absolute weight-average molecular weight to a relative weight-average molecular weight (absolute Mw/relative Mw) of the high-molecular-weight compound is 1.25 or more.

The high-molecular-weight compound of the present invention has an effect of improving the heat resistance of a thermoplastic resin and suppressing an increase in the viscosity of a solution to which the high-molecular-weight compound is added.

The high-molecular-weight compound of the present invention is a high-molecular-weight compound in which a plurality of polymer chains are linked through a divalent or higher-valent linking group.

A lower limit value of a ratio (absolute Mw/relative Mw) of an absolute weight-average molecular weight (hereinafter simply referred to as an "absolute Mw") with respect to a relative weight-average molecular weight (hereinafter also simply referred to as a "relative Mw") of the high-molecular-weight compound of the present invention is 1.25 or more, preferably 1.27 or more, and more preferably 1.29 or more.

When the ratio (absolute Mw/relative Mw) is the lower limit value or more, it is possible to suppress an increase in the viscosity of a solution to which the high-molecular-weight compound of the present invention is added.

An upper limit value of the ratio (absolute Mw/relative Mw) is not particularly limited, but is usually 3.00 or less, preferably 2.10 or less, more preferably 2.00 or less, still more preferably 1.95 or less, and even still more preferably 1.90 or less.

When the ratio (absolute Mw/relative Mw) is the upper limit value or less, the heat resistance of a resin composition obtained by adding the high-molecular-weight compound of the present invention to a thermoplastic resin is excellent.

A lower limit value of the relative Mw of the high-molecular-weight compound of the present invention is not particularly limited, but is preferably 1,000 or more, more preferably 1,500 or more, still more preferably 5,000 or more, even still more preferably 10,000 or more, even still more further preferably 20,000 or more, and particularly preferably 40,000 or more.

An upper limit value of the relative Mw of the high-molecular-weight compound of the present invention is not particularly limited, but is preferably 2,000,000 or less, more preferably 1,800,000 or less, still more preferably 1,500,000 or less, even still more preferably 1,200,000 or less, even still more further preferably 800,000 or less, and particularly preferably 500,000 or less.

Furthermore, the relative Mw of the high-molecular-weight compound of the present invention is a polymethyl methacrylate-equivalent value measured by gel permeation chromatography (GPC). Specifically, the relative Mw of the high-molecular-weight compound of the present invention is a value calculated by a method described in Examples which will be described later.

A lower limit value of the absolute Mw of the high-molecular-weight compound of the present invention is not particularly limited, but is preferably 1,250 or more, more preferably 1,500 or more, still more preferably 5,000 or more, even still more preferably 10,000 or more, even still more further preferably 20,000 or more, and particularly preferably 40,000 or more.

An upper limit value of the absolute Mw of the high-molecular-weight compound of the present invention is not particularly limited, but is preferably 2,000,000 or less, more preferably 1,800,000 or less, still more preferably 1,500,000 or less, even still more preferably 1,200,000 or less, even still more further preferably 800,000 or less, and particularly preferably 500,000 or less.

Furthermore, the absolute Mw of the high-molecular-weight compound means a molecular weight measured by gel permeation chromatography (GPC) and a light scattering detector, and specifically, a value calculated by the method described in Examples which will be described later.

The divalent or higher-valent linking group (hereinafter also simply referred to as a "linking group") has a thiol group (—SH) and at least one of a thioether structure and a thiourethane structure. The linking group may have both of the thioether structure and the thiourethane structure.

The "linking group" in the present invention means a moiety through which a plurality of polymer chains are linked in a high-molecular-weight compound. The plurality of polymer chains may be the same as or different from each other. The polymer chain is usually formed of repeating units which will be described later. In addition, the polymer chain may be a homopolymer or a copolymer.

The high-molecular-weight compound of the present invention has an effect of improving the heat resistance when the high-molecular-weight compound is added to a thermoplastic resin. A reason therefor is presumed to be as follows.

In a resin composition to which the high-molecular-weight compound of the present invention is added, even when the thermoplastic resin starts to be thermally decomposed, radicals generated by the decomposition are consumed by a chain transfer reaction of a thiol group contained in the high-molecular-weight compound. Therefore, the thermal decomposition of the thermoplastic resin stops quickly. In addition, when the high-molecular-weight compound starts to be thermally decomposed, the thermal decomposition stops with the cleavage of an S—C bond of a thioether structure or a thiourethane structure as an end point. Thus, the components of the high-molecular-weight compound which has been decomposed remain in the resin composition without volatilization. Therefore, an effect of improving the heat resistance of a thiol group of the high-molecular-weight compound is continuously sufficiently exhibited.

As described above, according to the high-molecular-weight compound of the present invention, an effect of improving the heat resistance of a thermoplastic resin can be obtained. The high-molecular-weight compound is effective even when it is added in a small amount.

In a related art, when a compound having thiol groups is reacted with another compound, a trace amount of unreacted thiol groups may remain unintentionally in the product. In contrast, the present invention has an effect that both of heat resistance and handleability can be achieved by intentionally leaving thiol groups.

Although the linking group has a thiol group, the high-molecular-weight compound of the present invention preferably has one or more thiol groups, more preferably two or more, and still more preferably five or more per molecule from the viewpoint of an effect of improving the heat resistance.

An upper limit value of the number of the thiol groups per molecule of the high-molecular-weight compound of the present invention is not particularly limited, but is preferably 300 or less. When the number of thiol groups per molecule of the high-molecular-weight compound of the present invention is the upper limit value or less, the inhibition of an effect of suppressing thermal decomposition due to a side reaction is suppressed. Therefore, the effect of improving the heat resistance is further improved.

The thiol groups can be quantified by, for example, a color identification test using an Ellman's reagent, a redox titration method, or the like. The color identification test using an Ellman's reagent is performed by the following method. First, an Ellman's reagent and a polymer are each dissolved to 4 mg/mL and 50 mg/mL, respectively, mixed at a volume ratio of 1:2, and left to stand for 1 to 3 hours, and then the mixed solution is measured by an ultraviolet spectrophotometer. Thus, the number of thiol groups can be calculated from the height of a peak having a maximum value at 450 nm to 550 nm.

The linking group is preferably a divalent or higher-valent group derived from a chain transfer agent (F) described later.

The chain transfer agent (F) has a moiety derived from a polyfunctional thiol compound (A) and a moiety derived from a compound (B) having a reactive group that reacts with a thiol group (hereinafter simply referred to as a "compound (B)").

The chain transfer agent (F) is a compound which has at least a thioether structure and a thiourethane structure formed by reacting a thiol group of the polyfunctional thiol compound (A) and a reactive group that reacts with a thiol group, of the compound (B), and has a plurality of thiol groups. The chain transfer agent (F) may have both of the thioether structure and the thiourethane structure. In addition, the chain transfer agent (F) may be a mixture of a plurality of different compounds.

For example, a high-molecular-weight compound can be obtained by reacting a polyfunctional thiol compound (A) with a compound (B) having a reactive group that reacts with a thiol group to obtain a chain transfer agent (F) having a thiol group, and polymerizing vinyl-based compounds in the presence of the chain transfer agent (F) and a radical polymerization initiator.

That is, the high-molecular-weight compound having the linking group according to the present invention is generated by performing radical polymerization of vinyl-based compounds using the chain transfer agent (F), and making a part of the plurality of thiol groups contained in the chain transfer agent (F) serve as a starting point for the growth of a polymer chain so that the thiol groups are bonded to the polymer chain and the residual thiol groups remain unreacted.

The polyfunctional thiol compound (A) is a compound having at least two thiol groups in a molecule thereof.

Examples of the polyfunctional thiol compound (A) include an aliphatic polythiol compound and an aromatic polythiol compound.

Examples of the aliphatic polythiol compound include an aliphatic polythiol compound having no sulfur atom other than a thiol group and an aliphatic polythiol compound having a sulfur atom other than a thiol group.

Examples of the aromatic polythiol compound include an aromatic polythiol compound having no sulfur atom other than a thiol group and an aromatic polythiol compound having a sulfur atom other than a thiol group.

Examples of the aliphatic polythiol compound having no sulfur atom other than a thiol group include methanedithiol, 1,2-ethanedithiol, 1,1-propanedithiol, 1,2-propanedithiol, 1,3-propanedithiol, 2,2-propanedithiol, 1,6-hexanedithiol, 1,2,3-propanetrithiol, 1,1-cyclohexanedithiol, 1,2-cyclohexanedithiol, 2,2-dimethylpropane-1,3-dithiol, 3,4-dimethoxybutane-1,2-dithiol, 2-methylcyclohexane-2,3-dithiol, 1,1-bis(mercaptomethyl)cyclohexane, thiomalic acid bis(2-mercaptoethyl ester), 2,3-dimercapto-1-propanol (2-mercaptoacetate), 2,3-dimercapto-1-propanol (3-mercaptopropionate), 2,3-dimercapto-1-propanol (3-mercaptobutyrate), diethylene glycol bis(2-mercaptoacetate), diethylene glycol bis(3-mercaptopropionate), diethylene glycol bis(3-mercaptobutyrate), 1,2-dimercaptopropylmethyl ether, 2,3-dimercaptopropylmethyl ether, 2,2-bis(mercaptomethyl)-1,3-propanedithiol, bis(2-mercaptoethyl)ether, ethylene glycol bis(2-mercaptoacetate), ethylene glycol bis(3-mercaptopropionate), ethylene glycol bis(3-mercaptobutyrate), tetraethylene glycol bis(3-mercaptopropionate), trimethylolpropane bis(2-mercaptoacetate), trimethylolpropane bis(3-mercaptopropionate), trimethylolpropane bis(3-mercaptobutyrate), pentaerythritol tetrakis(2-mercaptoacetate) (also referred to as pentaerythritol tetrakisthioglycolate), pentaerythritol tetrakis(3-mercaptopropionate), pentaerythritol tetrakis(3-mercaptobutyrate), tetrakis(mercaptomethyl)methane, dipentaerythritol hexakis(2-mercaptoacetate), dipentaerythritol hexakis(3-mercaptopropionate), and dipentaerythritol hexakis(3-mercaptobutyrate).

Examples of the aliphatic polythiol compound having a sulfur atom other than a thiol group include bis(mercaptomethyl) sulfide, bis(mercaptomethyl) disulfide, bis(mercaptoethyl) sulfide, bis(mercaptoethyl) disulfide, bis(mercaptopropyl) sulfide, bis(mercaptomethylthio)methane, bis(2-mercaptoethylthio)methane, bis(3-mercaptopropylthio) methane, 1,2-bis(mercaptomethylthio)ethane, 1,2-bis(2-mercaptoethylthio)ethane, 1,2-bis(3-mercaptopropyl) ethane, 1,3-bis(mercaptomethylthio)propane, 1,3-bis(2-mercaptoethylthio)propane, 1,3-bis(3-mercaptopropylthio) propane, 1,2,3-tris(mercaptomethylthio)propane, 1,2,3-tris(2-mercaptoethylthio)propane, 1,2,3-tris(3-mercaptopropylthio)propane, 1,2-bis[(2-mercaptoethyl) thio]-3-mercaptopropane, 4-mercaptomethyl-3,6-dithia-1,8-octanedithiol, 4,8-dimercaptomethyl-1,11-mercapto-3,6,9-trithiaundecane, 4,7-dimercaptomethyl-1,11-mercapto-3,6,9-trithiaundecane, 5,7-dimercaptomethyl-1,11-mercapto-3,6,9-trithiaundecane, tetrakis(mercaptomethylthiomethyl) methane, tetrakis(2-mercaptoethylthiomethyl)methane, tetrakis(3-mercaptopropylthiomethyl)methane, bis(2,3-dimercaptopropyl)sulfide, bis(1,3-dimercaptopropyl)sulfide, 2,5-dimercapto-1,4-dithiane, 2,5-dimercaptomethyl-1,4-dithiane, 2,5-dimercaptomethyl-2,5-dimethyl-1,4-dithiane, bis(mercaptomethyl) disulfide, bis(mercaptoethyl) disulfide, and bis(mercaptopropyl) disulfide.

In addition, examples of the aliphatic polythiol compound having a sulfur atom other than a thiol group include hydroxymethyl sulfide bis(2-mercaptoacetate), hydroxymethyl sulfide bis(3-mercaptopropionate), hydroxymethyl sulfide bis(3-mercaptobutyrate), hydroxyethyl sulfide bis(2-mercaptoacetate), hydroxyethyl sulfide bis(3-mercaptopropionate), hydroxyethyl sulfide bis(3-mercaptobutyrate), hydroxypropyl sulfide bis(2-mercaptoacetate), hydroxypropyl sulfide bis(3-mercaptopropionate), hydroxypropyl sulfide bis(3-mercaptobutyrate), hydroxymethyl disulfide bis(2-mercaptoacetate), hydroxymethyl disulfide bis(3-mercaptopropionate), hydroxymethyl disulfide bis(3-mercaptobutyrate), hydroxyethyl disulfide bis(2-mercaptoacetate), hydroxyethyl disulfide bis(3-mercaptopropionate), hydroxyethyl disulfide bis(3-mercaptobutyrate), hydroxypropyl disulfide bis(2-mercaptoacetate), hydroxypropyl disulfide bis(3-mercaptopropionate), hydroxypropyl disulfide bis(3-mercaptobutyrate), 2-mercaptoethyl ether bis(2-mercaptoacetate), 2-mercaptoethyl ether bis(3-mercaptopropionate), 2-mercaptoethyl ether bis(3-mercaptobutyrate), 1,4-dithiane-2,5-diol bis(2-mercaptoacetate), 1,4-dithiane-2,5-diol bis(3-mercaptopropionate), 1,4-dithiane-2,5-diol bis(3-mercaptobutyrate), thiodiglycolic acid bis(2-mercaptoethyl ester), thiodipropionic acid bis(2-mercaptoethyl ester), thiodibutanoic acid bis(2-mercaptoethyl ester), 4,4-thiodibutyric acid bis(2-mercaptoethyl ester), dithiodiglycolic acid bis(2-mercaptoethyl ester), dithiodipropionic acid bis(2-mercaptoethyl ester), dithiodibutanoic acid bis(2-mercaptoethyl ester), 4,4-dithiodibutyric acid bis(2-mercaptoethyl ester), thiodiglycolic acid bis(2,3-dimercaptopropyl ester), thiodipropionic acid bis(2,3-dimercaptopropyl ester), thiodibutanoic acid bis(2,3-dimercaptopropyl ester), dithioglycolic acid bis(2,3-dimercaptopropyl ester), dithiodipropionic acid bis(2,3-dimercaptopropyl ester), and dithiodibutanoic acid bis(2,3-dimercaptopropyl ester).

Examples of the aromatic polythiol compound having no sulfur atom other than a thiol group include 1,2-dimercaptobenzene, 1,3-dimercaptobenzene, 1,4-dimercaptobenzene, 1,2-bis(mercaptomethyl)benzene, 1,3-bis(mercaptomethyl)benzene, 1,4-bis(mercaptomethyl)benzene, 1,2-bis(mercaptoethyl)benzene, 1,3-bis(mercaptoethyl)benzene, 1,4-bis(mercaptoethyl)benzene, 1,2,3-trimercaptobenzene, 1,2,4-trimercaptobenzene, 1,3,5-trimercaptobenzene, 1,2,3-tris(mercaptomethyl)benzene, 1,2,4-tris(mercaptomethyl)benzene, 1,3,5-tris(mercaptomethyl)benzene, 1,2,3-tris(mercaptoethyl)benzene, 1,2,4-tris(mercaptoethyl)benzene, 1,3,5-tris(mercaptoethyl)benzene, 2,5-toluenedithiol, 3,4-toluenedithiol, 1,3-di(p-methoxyphenyl)propane-2,2-dithiol, 1,3-diphenylpropane-2,2-dithiol, phenylmethane-1,1-dithiol, and 2,4-di(p-mercaptophenyl)pentane.

Examples of the aromatic polythiol compound having a sulfur atom other than a thiol group include 1,2-bis(mercaptoethylthio)benzene, 1,3-bis(mercaptoethylthio)benzene, 1,4-bis(mercaptoethylthio)benzene, 1,2,3-tris(mercaptomethylthio)benzene, 1,2,4-tris(mercaptomethylthio)benzene, 1,3,5-tris(mercaptomethylthio)benzene, 1,2,3-tris(mercaptoethylthio)benzene, 1,2,4-tris(mercaptoethylthio)benzene, and 1,3,5-tris(mercaptoethylthio)benzene.

The polyfunctional thiol compound (A) used in the present invention is not particularly limited, but the aliphatic polythiol compound is preferable, and from the viewpoint of suppressing the decomposition of a linking group due to chain transfer, an aliphatic polythiol having no disulfide bond other than a thiol group is more preferable, and an aliphatic polythiol compound having no sulfur atom other than a thiol group is still more preferable.

A lower limit value of the average number of thiol groups per molecule of the polyfunctional thiol compound (A) is not particularly limited, but is preferably more than 1.5, more preferably 2 or more, and still more preferably 2.5 or more.

On the other hand, an upper limit value of the average number of thiol groups per molecule of the polyfunctional thiol compound (A) is not particularly limited, but is preferably 8 or less, more preferably 6 or less, and still more preferably 5 or less.

As the polyfunctional thiol compound (A), a polyfunctional thiol compound having an ester in a molecule thereof is preferable.

As the polyfunctional thiol compound having an ester in a molecule thereof, an aliphatic polythiol compound having an ester in a molecule thereof is preferable, an aliphatic polythiol compound having an ester in a molecule thereof and having no disulfide bond other than a thiol group is more preferable, and an aliphatic polythiol compound having an ester in a molecule thereof and having no sulfur atom other than a thiol group is still more preferable.

Examples of the polyfunctional thiol compound (A) include pentaerythritol tetrakis(3-mercaptopropionate) (PEMP), pentaerythritol tetrakis(2-mercaptoacetate) (PEMA), dipentaerythritol hexakis(3-mercaptopropionate) (DPMP), tetraethylene glycol bis(3-mercaptopropionate) (EGMP), and pentaerythritol tetrakis(3-mercaptobutyrate).

The polyfunctional thiol compound (A) may be used alone or in combination of two or more kinds thereof.

A lower limit value of the molecular weight of the polyfunctional thiol compound (A) is not particularly limited, but is preferably 80 or more, and more preferably 300 or more.

When the molecular weight of the polyfunctional thiol compound (A) is the lower limit value or more, difficulty in handling due to odor is more easily solved.

On the other hand, an upper limit value of the molecular weight of the polyfunctional thiol compound (A) is not particularly limited, but is preferably 2,000 or less, and more preferably 800 or less.

When the molecular weight of the polyfunctional thiol compound (A) is the upper limit value or less, difficulty in handling due to an increase in viscosity is more easily solved.

Furthermore, the molecular weight of the polyfunctional thiol compound (A) is a molecular weight that is theoretically calculated based on a chemical structure thereof.

The compound (B) is a compound having at least one reactive group (hereinafter also simply referred to as a "reactive group") that reacts with a thiol group in a molecule thereof.

The reactive group is, for example, a functional group capable of reacting with a thiol group to form an S—C bond.

Examples of the reactive group include a (meth)acrylate group, a vinyl group (provided that a vinyl group contained in a (meth)acrylate group is excluded), a glycidyl group, and an isocyanate group.

As the reactive group, one or more selected from the group consisting of an acrylate group, a glycidyl group, and an isocyanate group are preferable from the viewpoint of a high addition reactivity with a thiol group.

Furthermore, in the present specification, "(meth)acrylate" means acrylate or methacrylate.

A thioether structure (R—S—R') is formed by reacting a thiol group of the polyfunctional thiol compound (A) with a (meth)acrylate group, a vinyl group, or a glycidyl group of the compound (B). A thiourethane structure (R—S—C(=O)—NH—R' or R—S—C(=S)—NH—R') is formed by reacting a thiol group of the polyfunctional thiol compound (A) with an isocyanate group of the compound (B). R and R' each represents any organic group.

As a result, the polyfunctional thiol compound (A) is bonded via the compound (B), and many thiol groups can be present at a distance in one molecule. By using this as the chain transfer agent (F), it is less likely to be affected by the steric hindrance of a polymer chain thus generated, and a high-molecular-weight compound having a plurality of polymer chains can be produced. That is, it is possible to produce a high-molecular-weight compound having a high degree of branching, which is difficult to produce with the polyfunctional thiol compound (A) alone.

Examples of the compound (B) include an acrylic acid, a methacrylic acid, mono(meth)acrylate-based compounds, poly(meth)acrylate-based compounds, monovinyl-based compounds, polyvinyl-based compounds, monoepoxy-based compounds, polyepoxy-based compounds, monoisocyanate-based compounds, and polyisocyanate-based compounds.

Examples of the mono(meth)acrylate-based compounds include alkyl (meth)acrylate, hydroxyethyl (meth)acrylate, hydroxypropyl (meth)acrylate, and glycidyl (meth)acrylate, methoxyethyl (meth)acrylate, ethoxyethyl (meth)acrylate, and ethoxyethoxyethyl (meth)acrylate, which has a linear or branched alkyl group having 1 to 30 carbon atoms.

Examples of the poly(meth)acrylate-based compounds include a diester compound obtained by reacting a diol with an acrylic acid, a polyester compound obtained by reacting a compound having three or more hydroxyl groups per molecule with an acrylic acid, and a compound obtained by reacting a compound having two or more epoxy groups with an acrylic acid.

Specific examples of the diester compound obtained by reacting a diol with an acrylic acid include ethylene glycol diacrylate, polyethylene glycol diacrylate, propylene glycol diacrylate, polypropylene glycol diacrylate, 1,3-butylene glycol diacrylate, 1,6-hexanediol diacrylate, 1,9-nonanediol di(meth)acrylate, 1,10-decanediol di(meth)acrylate, neopentyl glycol diacrylate, tetraethylene glycol diacrylate, 2-hydroxy-1,3-diacryloxypropane, 2,2-bis[4-(acryloxyethoxy)phenyl]propane, 2,2-bis[4-(acryloxy/polyethoxy)phenyl]propane, bis[4-(acryloxy/ethoxy)phenyl]methane, and 2-hydroxy-1-acryloxy-3-acryloxypropane.

Specific examples of the polyester compound obtained by reacting a compound having three or more hydroxyl groups per molecule with an acrylic acid include trimethylolpropane triacrylate, tetramethylol triacrylate, pentaerythritol tetrakisacrylate (tetramethylolmethane tetraacrylate), and dipentaerythritol hexakisacrylate.

Specific examples of the compound obtained by reacting a compound having two or more epoxy groups with an acrylic acid are bisphenol A diglycidyl ether and bisphenol F diglycidyl ether.

Examples of the monovinyl-based compound include styrene-based compounds, vinyl ether-based compounds, fumaric acid, a monoalkyl ester of fumaric acid, a dialkyl ester of fumaric acid, maleic acid, a monoalkyl ester of maleic acid, a dialkyl ester of maleic acid, itaconic acid, a monoalkyl ester of itaconic acid, a dialkyl ester of itaconic acid, acrylonitrile, methacrylonitrile, vinyl chloride, vinylidene chloride, vinyl acetate, vinyl ketone, vinyl pyridine, and vinyl carbazole.

Specific examples of the styrene-based compounds are α-methylstyrene, vinyl toluene, and styrene.

Specific examples of the vinyl ether-based compounds are methyl vinyl ether, ethyl vinyl ether, and isobutyl vinyl ether.

Examples of the polyvinyl-based compounds include butadiene, isoprene and allyl acrylate, and a compound having a plurality of structures equivalent to those of the monovinyl-based compounds in one molecule.

Examples of the compound having a plurality of structures equivalent to those of the monovinyl-based compounds in one molecule include divinylbenzene.

Examples of the monoepoxy-based compound include phenyl glycidyl ether, cresyl glycidyl ether, p-t-butylphenyl glycidyl ether, butyl glycidyl ether, alcohol glycidyl ether having 12 to 14 carbon atoms, butane diglycidyl ether, and hexane diglycidyl ether, cyclohexane dimethyl diglycidyl ether, and glycidyl ether based on polyethylene glycol or polypropylene glycol.

Examples of the polyepoxy-based compounds include neopentyl glycol diglycidyl ether, a bisphenol type epoxy resin, a novolac type epoxy resin, and a compound having a plurality of glycidyl groups.

Examples of the bisphenol type epoxy resin include a bisphenol A type epoxy resin, a bisphenol F type epoxy resin, and a bisphenol A/bisphenol F copolymer type epoxy resin.

Examples of the novolac type epoxy resin include a cresol novolac type epoxy resin and a phenol novolac type epoxy resin.

Examples of the compound having a plurality of glycidyl groups include triglycidyl aminophenol, biphenyl diglycidyl ether, triglycidyl isocyanurate, polyglycidyl (meth)acrylate, and a copolymer of glycidyl (meth)acrylate and a vinyl-based monomer copolymerizable therewith.

Examples of the monoisocyanate-based compounds include n-butyl isocyanate, isopropyl isocyanate, phenyl isocyanate, and benzyl isocyanate.

Examples of the polyisocyanate-based compounds include diisocyanate, modified isocyanate, and triisocyanate.

Specific examples of the diisocyanate include 1,2-diisocyanatobenzene, 1,3-diisocyanatobenzene, 1,4-diisocyanatobenzene, trimethyl hexamethylene diisocyanate, 2,4-diisocyanatotoluene, ethylphenylene diisocyanate, isopropylphenylene diisocyanate, dimethylphenylene diisocyanate, diethylphenylene diisocyanate, diisopropylphenylene diisocyanate, biphenyl diisocyanate, toluidine diisocyanate, 4,4'-methylenebis(phenyl isocyanate), 4,4'-methylenebis(2-methylphenyl isocyanate), bibenzyl-4,4'-diisocyanate, bis(isocyanatophenyl)ethylene, isophorone diisocyanate, 1,4-tetramethylene diisocyanate, 1,6-hexamethylene diisocyanate, cyclohexane diisocyanate, methylcyclohexane diisocyanate, 4,4'-methylenebis(cyclohexyl isocyanate), 4,4'-methylenebis(2-methylcyclohexyl isocyanate), 3,8-bis(isocyanatomethyl)tricyclodecane, 3,9-bis(isocyanatomethyl)tricyclodecane, 4,8-bis(isocyanatomethyl)tricyclodecane, and 4,9-bis(isocyanatomethyl)tricyclodecane.

Examples of the modified isocyanate include a biuret type or an isocyanurate type of a diisocyanate.

Specific examples of the triisocyanate include triisocyanatononane, triphenylmethane triisocyanate, trimethylbenzene triisocyanate, benzene triisocyanate, and toluene triisocyanate.

Other examples of the isocyanate compounds include an isocyanate compound whose chain length has been extended with either one or both of a polyamine and a polyol.

As the compound (B), 1,6-hexanediol diacrylate, ethylhexyl acrylate, trimethylolpropane triacrylate, neopentyl glycol diglycidyl ether, trimethyl hexamethylene diisocyanate, tetraethylene glycol diacrylate, or the like is preferable.

The compound (B) may be used alone or in combination of two or more kinds thereof.

A lower limit value of the number of reactive groups per molecule of the compound (B) is not particularly limited, but is preferably 1 or more.

An upper limit value of the number of reactive groups per molecule of the compound (B) is not particularly limited, but is preferably 8 or less, and more preferably 6 or less.

When only one compound (B) is used, the number of reactive groups per molecule of the compound (B) is preferably 2 or more.

The average number of reactive groups per molecule of the compound (B) is preferably 1.2 to 8, more preferably 1.3 to 6, and still more preferably 1.5 to 3 from the viewpoint that the high-molecular-weight compound of the present invention can be easily obtained.

A lower limit value of the molecular weight of the compound (B) is not particularly limited, but is preferably 80 or more, more preferably 180 or more, and still more preferably 200 or more.

When the molecular weight of the compound (B) is the lower limit value or more, the solubility in a solvent when the compound (B) is used as a chain transfer agent (F) for polymerization is further improved and difficulty in handling due to volatilization is more easily solved.

On the other hand, an upper limit value of the molecular weight of the compound (B) is not particularly limited, but is preferably 2,000 or less, more preferably 800 or less, and still more preferably 400 or less.

When the molecular weight of the compound (B) is the upper limit value or less, difficulty in handling due to an increase in viscosity is more easily solved.

Furthermore, the molecular weight of the compound (B) is a molecular weight theoretically calculated based on a chemical structure thereof.

The linking group has at least one of a thioether structure and a thiourethane structure.

When the linking group has the thioether structure, it preferably has a structure represented by Formula (1) from the viewpoint that the heat resistance is improved.

In addition, when the linking group has the thiourethane structure, it preferably has a structure represented by Formula (2) from the viewpoint that the heat resistance is improved.

The structure represented by Formula (1) can be formed, for example, by reacting a thiol group of the polyfunctional thiol compound (A) with a (meth)acrylate-based group of the mono(meth)acrylate-based compound or the poly(meth)acrylate compound.

In addition, the structure represented by Formula (2) can be formed, for example, by reacting a thiol group of the polyfunctional thiol compound (A) with an isocyanate group of the monoisocyanate-based compound or the polyisocyanate-based compound.

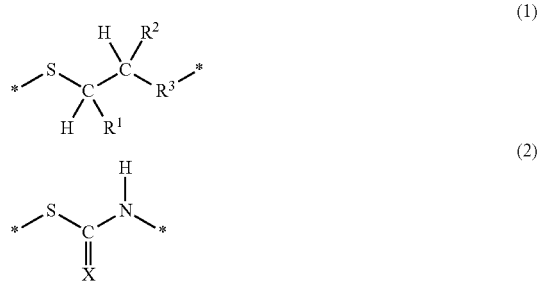

In Formula (1), $R^1$ and $R^2$ are each independently a hydrogen atom, a monovalent hydrocarbon group, a hydroxyl group, or a monovalent electron-withdrawing group.

The monovalent hydrocarbon group is not particularly limited, but is preferably an alkyl group, more preferably an alkyl group having 6 or less carbon atoms, still more preferably a methyl group or an ethyl group, and even still more preferably the methyl group.

The monovalent electron-withdrawing group is not particularly limited, but is preferably a halogen atom such as a fluorine atom and a chlorine atom, a halogenated hydrocarbon group such as a trifluoromethyl group, and an alkoxycarbonyl group (—COOR) such as a carboxyl group (—COOH) and a methoxycarbonyl group, an aryloxycarbonyl group (—COOR) such as a phenoxycarbonyl group, an acyl group (—COR) such as an acetyl group, a cyano group (—CN), an aryl group or a substitution product thereof, a nitro group (—NO$_2$), a sulfo group (—SO$_3$H), an alkoxysulfonyl group (—SO$_3$R), an alkanesulfonyl group (—SO$_2$R), an alkanesulfinyl group (—SOR), a carbamoyl group (—CONH$_2$), or an alkylcarbamoyl group (—CONHR).

$R^1$ is preferably the hydrogen atom. In addition, $R^2$ is preferably the hydrogen atom, the methyl group, or the hydroxyl group.

In Formula (1), $R^3$ is an oxygen atom, a divalent hydrocarbon group, or a divalent electron-withdrawing group.

The divalent hydrocarbon group is not particularly limited, but is preferably an alkylene group, more preferably an alkylene group having 6 or less carbon atoms, still more preferably a methylene group or an ethylene group, and even still more preferably the methylene group.

The divalent electron-withdrawing group is not particularly limited, but is preferably a carbonyl group (—CO—), an ester group (—COO—), a sulfo group (—SO$_3$—), a sulfonyl group (—SO$_2$—), a sulfinyl group (—SO—), an amide group (—CONH—), an aryl group or a substitution product thereof, or the like.

$R^3$ is preferably the methylene group or the ester group.

In Formula (1), -* is a bond.

In Formula (1), a combination in which $R^1$ is a hydrogen atom, $R^2$ is a hydrogen atom, a methyl group, or a hydroxyl group, and $R^3$ is a methylene group or an ester group is preferable, and a combination in which $R^1$ is a hydrogen atom and $R^2$ is a hydroxyl group, and $R^3$ is a methylene group, or a combination in which $R^1$ is a hydrogen atom, $R^2$ is a hydrogen atom or a methyl group, and $R^3$ is an ester group is more preferable.

In Formula (2), X is an oxygen atom or a sulfur atom, and is preferably the oxygen atom.

In Formula (2), -* is a bond.

The linking group preferably has a thioether structure, and more preferably has the structure represented by Formula (1) from the viewpoints of excellent long-term thermal stability, easy production, and acquisition of various compounds. When the linking group has the thioether structure, the high-molecular-weight compound of the present invention tends to have excellent long-term thermal stability since the thioether structure has a peroxide decomposition capability in a system.

In addition, the linking group preferably has a thiourethane structure. When the linking group has the thiourethane structure, the high-molecular-weight compound of the present invention tends to have excellent dynamic characteristics due to a high cohesive force.

The chain transfer agent (F) can be obtained, for example, by subjecting the polyfunctional thiol compound (A) and the compound (B) to an addition-polymerization reaction.

In the addition-polymerization reaction of the polyfunctional thiol compound (A) and the compound (B), a solvent may or may not be used. When a solvent is used in the addition-polymerization reaction, the solvent is not particularly limited, and for example, methyl ethyl ketone, tetrahydrofuran (THF), or toluene can be used. It should be noted that when a solvent is used in the addition-polymerization reaction, the amount of solvent at a start of the addition reaction in order to improve the reaction efficiency is preferably 50% by mass or less, more preferably 30% by mass, or less, and still more preferably 10% by mass or less, with respect to the total mass of the polyfunctional thiol compound (A) and the compound (B), and still more preferably, the solvent is not used.

A lower limit of the molar ratio (reactive groups/thiol groups) of a total amount of thiol groups of the polyfunctional thiol compound (A) used in the addition-polymerization reaction of the polyfunctional thiol compound (A) and the compound (B) to a total amount of reactive groups of the compound (B) is not particularly limited, but is preferably ⅛ or more.

On the other hand, an upper limit of the molar ratio (reactive groups/thiol groups) is not particularly limited, but is preferably 1/1.2 or less, more preferably 1/1.5 or less, and still more preferably ⅓ or less.

When the molar ratio (reactive groups/thiol groups) is the lower limit value or more and the upper limit value or less, a chain transfer agent (F) having a plurality of thiol groups can be easily obtained.

The external temperature during the addition-polymerization reaction of the polyfunctional thiol compound (A) and the compound (B) is not particularly limited, but is preferably 10° C. to 80° C., more preferably 10° C. to 50° C., and still more preferably 25° C. to 50° C. The external temperature during the reaction means, for example, a set temperature of a water bath or an oil bath that heats a reaction vessel.

A reaction time of the addition-polymerization reaction between the polyfunctional thiol compound (A) and the compound (B) is preferably 0.05 to 10 hours, and more preferably 2 to 5 hours. When the reaction time is 0.05 hours or more, it is easy to suppress reaction raw materials from remaining unreacted.

The addition-polymerization reaction between the polyfunctional thiol compound (A) and the compound (B) is preferably carried out in the presence of a catalyst (C). The catalyst (C) is not particularly limited, but is preferably a phosphine compound. The phosphine compound provides phosphine enolate, which is a zwitterionic intermediate, by nucleophilically attacking a reactive group of the compound (B). Since phosphine enolate is highly basic, it extracts a proton from the thiol group to form phosphonium, and produces a thiolate anion at the same time. Subsequently, a thiolate anion is nucleophilically added to the reactive group, and a proton is extracted from another thiol group or phosphonium to make the thiol group and the reactive group bond to each other.

Examples of the phosphine compound include phosphines and diphosphines.

Specific examples of the phosphines include trimethylphosphine, triethylphosphine, tripropylphosphine, triisopropylphosphine, tri-n-butylphosphine, tri-t-butylphosphine, tri-n-octylphosphine, tricyclohexylphosphine, tribenzylphosphine, triphenylphosphine, diphenylmethylphosphine, dimethylphenylphosphine, diphenylcyclohexylphosphine, dicyclohexylphosphine, diethylphenylphosphine, tri-o-tolylphosphine, tri-m-tolylphosphine, tri-p-tolylphosphine, tri-2,4-xylylphosphine, tri-2,5-xylylphosphine, tri-3,5-xylylphosphine, tris(p-methoxyphenyl)phosphine, tris(p-t-butoxyphenyl)phosphine, di-t-butylphenylphosphine, [4-(N,N-dimethylamino)phenyl]di-t-butylphosphine, di-t-butyl(2-butenyl)phosphine, di-t-butyl(3-methyl-2-butenyl)phosphine, and trimesitylphosphine.

Specific examples of the diphosphines include 1,2-bis(dimethylphosphino)ethane, bis(diphenylphosphino)methane, 1,2-bis(diphenylphosphino)ethane, 1,2-bis(diphenylphosphino)propane, 1,3-bis(diphenylphosphino)propane, 1,4-bis(diphenylphosphino)butane, 2,3-bis(diphenylphosphino)butane, and 1,5-bis(diphenylphosphino)pentane.

The catalysts (C) may be used alone or in combination of two or more kinds thereof.

The amount of catalyst (C) to be used is preferably 0.001% to 10% by mass, more preferably 0.002% to 5% by mass, and still more preferably 0.004% to 3% by mass, with respect to 1 g of the polyfunctional thiol compound (A). When the amount of catalyst (C) to be used is the lower limit value of the range or more, a reaction easily proceeds, and when the amount is the upper limit value of the range or less, there is no influence of the residual catalyst.

The polymer chain in the high-molecular-weight compound of the present invention has a structural unit derived from a radically polymerizable monomer (D).

Examples of the radically polymerizable monomer (D) include the acrylic acid, the methacrylic acid, the mono(meth)acrylate-based compounds, the poly(meth)acrylate-based compounds, the monovinyl-based compounds, and the polyvinyl-based compounds exemplified in the compound (B).

The structural units derived from the radically polymerizable monomers (D) that form the polymer chain may be of one or more kinds.

The high-molecular-weight compound of the present invention can be obtained, for example, by radically polymerizing the radically polymerizable monomers (D) using a chain transfer agent (F).

The amount of chain transfer agent (F) to be used in the radical polymerization of the radically polymerizable monomers (D) is preferably 0.2 to 20 parts by mass, and more preferably 0.6 to 15 parts by mass, with respect to 100 parts by mass of the total amount of radically polymerizable monomers (D).

Examples of the form of the radical polymerization include solution polymerization, bulk polymerization, suspension polymerization, and emulsion polymerization.

Examples of a polymerization solvent to be used for the radical polymerization include aromatic hydrocarbon-based solvents (toluene, ethylbenzene, xylene, and the like), aliphatic hydrocarbon-based solvents (pentane, hexane, heptane, octane, cyclohexane, and the like), ketone-based solvents (acetone, methyl isobutyl ketone, methyl ethyl ketone, and the like), ester-based solvents (butyl acetate and the like), and alcohol-based solvents (methanol, ethanol, and the like).

The polymerization solvents may be of one or more kinds.

The amount of polymerization solvent to be used is preferably 50 to 500 parts by mass, and more preferably 100 to 300 parts by mass, with respect to 100 parts by mass of the total amount of radically polymerizable monomers (D).

Examples of a radical polymerization initiator to be used in the radical polymerization include peroxides such as dibenzoyl peroxide and tert-butyl permalate, and azo-based compounds such as 2,2'-azobisisobutyronitrile and azobisisovaleronitrile.

The radical polymerization initiators may be of one or more kinds.

The amount of radical polymerization initiator to be used is preferably 0.0001 to 10 parts by mass, and more preferably 0.001 to 1 part by mass, with respect to 100 parts by mass of the total amount of radically polymerizable monomers (D).

A polymerization temperature for the radical polymerization can be appropriately set, and is, for example, preferably −100° C. to 250° C. from the viewpoint that the polymerization temperature is suitable as an operating temperature range for the radical polymerization initiator.

A polymerization time for the radical polymerization can be appropriately set, and can be, for example, 0.5 to 48 hours.

As described above, in the high-molecular-weight compound of the present invention, a plurality of polymer chains are linked through a linking group, the linking group has a thiol group and at least one of a thioether structure and a thiourethane structure, and a ratio (absolute Mw/relative Mw) of the high-molecular-weight compound is controlled to be in a specific range. As a result, both of an effect of improving the heat resistance of a thermoplastic resin and an effect of suppressing an increase in the viscosity of a solution to which the high-molecular-weight compound is added can be achieved.

[Composition and Method for Producing Same]

The composition of the present invention is a composition including, as a main component, a compound (E) having a moiety derived from a polyfunctional thiol compound (A) and a moiety derived from a compound (B) having a reactive group that reacts with a thiol group, in which the composition satisfies Formulae (11) and (12), $$r \times (f_A - 1) \times (f_B - 1) < 1.2 \quad (11)$$

$$r = (f_B \times y)/(f_A \times x) \quad (12)$$

In Formula (11), $f_A$ is an average number of thiol groups per molecule of the polyfunctional thiol compound (A). $f_B$ is an average number of reactive groups per molecule of the compound (B). $f_A$ is 2.0 or more and $f_B$ is 1.2 or more. It should be noted that a case where only the compound (A) having two thiol groups and only the compound (B) having two reactive groups are used is excluded. r is a value calculated by Formula (12) when a molar ratio of the moiety derived from the polyfunctional thiol compound (A) to the moiety derived from the compound (B) is defined as x:y.

The composition of the present invention has excellent solubility in a polymerization solvent and a monomer, and can be suitably used for production of the high-molecular-weight compound as a chain transfer agent. In addition, the composition of the present invention has an effect of improving the heat resistance of a thermoplastic resin and suppressing an increase in the viscosity of a solution to which the composition is added.

The compound (E) may be a single compound satisfying Formulae (11) and (12), or may be a group of a plurality of compounds satisfying Formulae (11) and (12).

The composition of the present invention includes the compound (E) as a main component. That is, the compound (E) may be included in a largest amount in terms of mass ratio, and may include, for example, an unreacted polyfunctional thiol compound (A) or a compound (B) in addition to the compound (E).

The composition of the present invention includes the compound (E) in an amount of preferably 50% by mass or more, preferably 70% by mass or more, still more preferably 80% by mass or more, and even still more preferably 90% by mass or more, with respect to the total mass of the composition.

The compound (E) has a moiety derived from the polyfunctional thiol compound (A) and a moiety derived from the compound (B) having a reactive group that reacts with a thiol group.

In the compound (E), the moiety derived from the polyfunctional thiol compound (A) means a moiety formed based on the polyfunctional thiol compound (A) in a structure that is formed when the polyfunctional thiol compound (A) is reacted with the compound (B) having a reactive group that reacts with a thiol group.

Similarly, in compound (E), the moiety derived from compound (B) having a reactive group that reacts with a thiol group means a moiety formed based on the compound (B) in a structure that is formed when the polyfunctional thiol compound (A) reacts with the compound (B) having a reactive group that reacts with a thiol group.

Furthermore, in the present invention, the moiety derived from the polyfunctional thiol compound (A) may sometimes be referred to as a structural unit formed of the polyfunctional thiol compound (A).

In addition, in the present invention, the moiety derived from the compound (B) having a reactive group that reacts with a thiol group may be referred to as a structural unit formed of the compound (B) having a reactive group that reacts with a thiol group.

Examples of the thioether structure or the thiourethane structure include a moiety having the structure represented by Formula (1) or Formula (2) from the viewpoint of improving the heat resistance.

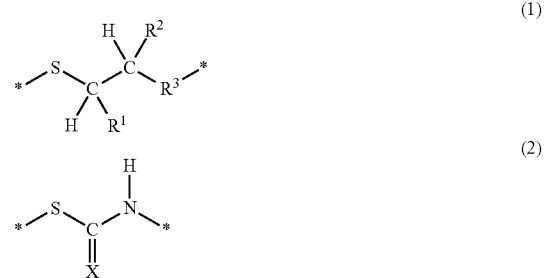

The compound (E) preferably has a thioether structure, and more preferably has the structure represented by Formula (1), from the viewpoint that production of the compound is easily performed and various compounds are easily obtained.

When the compound (E) has the thioether structure, a high-molecular-weight compound obtained by performing polymerization using the compound (E) as a chain transfer agent tends to have excellent long-term thermal stability.

In addition, when the compound (E) has the thioether structure, a high-molecular-weight compound obtained by performing polymerization using the compound (E) as a chain transfer agent tends to have excellent dynamic characteristics.

The compound (E) preferably has at least one thiol group per molecule.

A lower limit value of the average number of thiol groups per molecule of the compound (E) is not particularly limited, but is preferably 3 or more, and more preferably 4 or more.

On the other hand, an upper limit value of the average number of thiol groups per molecule of the compound (E) is not particularly limited, but is preferably 50 or less, and more preferably 30 or less.

When the average number of thiol groups per molecule of the compound (E) is the lower limit value or more, the number of branches of a polymer obtained when the composition of the present invention is used as a chain transfer agent is likely to be sufficient and there is also an effect of enhancing the heat resistance of the polymer.

When the average number of thiol groups per molecule of the compound (E) is the upper limit value or less, the solution viscosity of a polymer obtained when the composition of the present invention is used as a chain transfer agent can be reduced.

The description above can be applied as it is to the polyfunctional thiol compound (A) and the compound (B) having a reactive group that reacts with a thiol group.

The composition of the present invention satisfies Formulae (11) and (12).

$$r \times (f_A - 1) \times (f_B - 1) < 1.2 \quad (11)$$

$$r = (f_B \times y)/(f_A \times x) \quad (12)$$

In Formula (11), $f_A$ is an average number of thiol groups per molecule of the polyfunctional thiol compound (A). $f_B$ is an average number of reactive groups per molecule of the compound (B). $f_A$ is 2.0 or more and $f_B$ is 1.2 or more. It should be noted that a case where only the compound (A) having two thiol groups and only the compound (B) having two reactive groups are used is excluded. r is a value calculated by Formula (12) when a molar ratio of the moiety derived from the polyfunctional thiol compound (A) to the moiety derived from the compound (B) is defined as x:y.

The composition of the present invention has excellent solubility in a polymerization solvent and a monomer by satisfying Formulae (11) and (12). A reason thereof can be presumed to be as follows, for example. When each of the values of $(f_A-1)$ and $(f_B-1)$ in Formula (11) is small, the number of reaction points during the production of the composition is small. Therefore, the molecular weight of the composition does not increase excessively and the composition has excellent solubility. When the value of r is small, the number of thiol groups in the product increases, the number of branches of the composition increases, and the solubility is enhanced.

Furthermore, when it is intended to lower all of the respective values of r, $(f_A-1)$, and $(f_B-1)$, there is a great restriction in terms of raw materials for production and the like, but in the present invention, the raw materials for production of the composition and the like only need to be adjusted in consideration of setting Formula (11), that is, a product of $r \times (f_A-1) \times (f_B-1)$ to less than 1.2 and it is not necessary to lower all of the respective values. From this viewpoint, the present invention also has an advantage in that a degree of freedom in selecting raw materials and the like in the production of the composition is high.

The value of Formula (11) is 1.2 or less. The present inventors have found that in a composition including the compound (E), when Formula (11) is 1.2 or less, the solubility in a polymerization solvent or a monomer is excellent, and the composition is also suitable as a chain transfer agent. When the value of Formula (11) is more than 1.2, the composition is easily gelled or cured, does not dissolve in a solvent, and does not dissolve in another resin or the like.

An upper limit value of the value of Formula (11) is 1.2 or less, preferably 1.15 or less, and more preferably 1.1 or less. On the other hand, a lower limit value of the value of Formula (11) is not particularly limited, but is preferably 0.1 or more, and more preferably 0.3 or more. When the value of Formula (11) is the upper limit value of the range or less, the solubility in the polymerization solvent and the monomer is further improved. When the value of Formula (11) is the lower limit value of the range or more, the number of unreacted functional groups per molecule of the obtained compound (E) increases and the composition is easily used as a chain transfer agent. For example, when the composition of the present invention including the compound (E) is used as a chain transfer agent, the solution viscosity of a polymer thus obtained can be reduced and the handleability is enhanced.

The average number $f_A$ of the thiol groups per molecule of the polyfunctional thiol compound (A) has a lower limit value of 2.0 or more, preferably 2.5 or more, and more preferably 3.0 or more. On the other hand, an upper limit value of the average number $f_A$ of the thiol groups per molecule of the polyfunctional thiol compound (A) is not particularly limited, but is preferably 9.0 or less, and more preferably 6.0 or less, from the viewpoint of preventing the insolubilization of the polyfunctional thiol compound (A).

The lower limit value of the average number $f_B$ of the reactive groups per molecule of the compound (B) is 1.2 or more, preferably 1.3 or more, and more preferably 1.5 or more. On the other hand, an upper limit value of the average number $f_B$ of the reactive groups per molecule of the compound (B) is not particularly limited, but is preferably 6.0 or less, more preferably 4.0 or less, and still more preferably 3.0 or less, from the viewpoint of reducing the amount of unreacted thiol groups remaining in the product.

It should be noted that a case where only the compound (A) having two thiol groups and only the compound (B) having two reactive groups are used is excluded. That is, when only the polyfunctional thiol compound (A) having two thiol groups and the compound (B) having two reactive groups that react with thiol groups are reacted to each other, the obtained compound (E) is almost linear. Therefore, when the compound (E) is used as a chain transfer agent, the number of branches of the obtained polymer is insufficient.

In addition, a lower limit value of $f_A + f_B$ is not particularly limited, but is preferably more than 4.0, more preferably 4.5 or more, and still more preferably 5.0 or more. When $f_A + f_B$ is more than 4.0, the obtained compound (E) has more branches and the solubility of the composition is enhanced. An upper limit value of $f_A + f_B$ is not particularly limited, but is usually 12.0 or less, and preferably 10.0 or less.

A lower limit value of the ratio (x/y) of the number of moles x of the moiety derived from the polyfunctional thiol compound (A) to the number of moles y of the moiety derived from the compound (B) is not particularly limited, but is preferably 0.5 or more, more preferably 0.8 or more, and still more preferably 1.0 or more. On the other hand, an upper limit value of the ratio (x/y) is not particularly limited, but is preferably 8.0 or less, more preferably 6.0 or less, and still more preferably 4.0 or less.

It is preferable that the ratio (x/y) be the lower limit value or more and the upper limit value or less from the viewpoint of the number of branches of the compound (E) and the solubility. In addition, the compound (E) easily has a thiol group and is easily used as a chain transfer agent.

The relative Mw of the composition of the present invention is preferably 1,000 or more, more preferably 1,000 to 50,000, and still more preferably 2,000 to 20,000 from the viewpoint of the solubility and the like.

Furthermore, the relative Mw of the composition is a polymethyl methacrylate-equivalent value measured by gel permeation chromatography (GPC), and specifically means a value calculated by the method described later in Examples. In the differential molecular weight distribution obtained by GPC measurement of the composition of the present invention, a plurality of molecular weight peaks are typically observed in a region having a molecular weight of 1,000 or more. In this case, it is preferable that all of the plurality of molecular weight peaks be included in the range.

In the method for producing the composition of the present invention, it is preferable that the polyfunctional thiol compound (A) be reacted with the compound (B) having a reactive group that reacts with a thiol group under conditions satisfying Formulae (13) and (14).

$$r' \times (f_A - 1) \times (f_B - 1) < 1.2 \quad (13)$$

$$r' = (f_B \times y')/(f_A \times x') \quad (14)$$

In Formula (13), $f_A$ is an average number of thiol groups per molecule of the polyfunctional thiol compound (A). $f_B$ is an average number of reactive groups per molecule of the compound (B). $f_A$ is 2.0 or more and $f_B$ is 1.2 or more. It should be noted that a case where only the compound (A) having two thiol groups and only the compound (B) having two reactive groups are used is excluded, and r' is a value calculated by Formula (14) when a molar ratio of the polyfunctional thiol compound (A) to the compound (B) is x':y'.

x', y' and r' are values at the time of preparation of a reaction, but when the composition after the reaction is used as it is as a "composition including the compound (E)", x', y', and r' are each the same as x, y, and r.

Preferred ranges of $f_A$ and $f_B$ in Formula (13) are each the same as those of $f_A$ and $f_B$ in Formula (11), and a preferred range of $r' \times (f_A-1) \times (f_B-1)$ is also the same as that of $r \times (f_A-1) \times (f_B-1)$ in Formula (11).

In addition, preferred ratios of x' and y' are each the same as the preferred ratios of x and y in Formula (11), and a preferred value of r' is also the same as the preferred value of r in Formula (11).

Examples of the polyfunctional thiol compound (A) and the compound (B) include the polyfunctional thiol compound (A) and the compound (B), each as described above.

The obtained composition preferably includes the compound (E) as a main component. The composition may include the polyfunctional thiol compound (A) and the compound (B), each of which is unreacted.

With regard to the conditions of the present reaction, the above-described conditions for obtaining the chain transfer agent (F) by subjecting the polyfunctional thiol compound (A) and the compound (B) to an addition-polymerization reaction can be applied as they are.

In addition, the reaction is not particularly limited, but is preferably carried out in the presence of a catalyst (C). As the catalyst (C), the description above can be applied as it is.

In addition, the composition may be used in combination with additives such as a pigment, an ultraviolet absorber, an adhesion promoter, a release agent, a stabilizer, an antioxidant, a defoaming agent, a plasticizer, and a viscosity modifier, as necessary.

The amount of additive to be used is preferably less than 5% by mass, more preferably less than 3% by mass, and still more preferably less than 1% by mass, with respect to the total mass of the composition.

As described above, in the present invention, when the composition including the compound (E) satisfies the conditions, the number of branches is large, a crosslinkable polymer network is not formed, and the composition has excellent solubility in a polymerization solvent or a monomer.

The composition of the present invention can be suitably used as a chain transfer agent in a radical polymerization reaction system. Since a branched polymer produced using the composition of the present invention as a chain transfer agent has a large number of branches, the viscosity of a solution to which the branched polymer is added can be kept low even when the polymer has a high molecular weight. Therefore, for example, a paint to which the branched polymer is added can have both of an effect of improving the physical properties of a coating film, and paintability. In addition, the branched polymer also has an effect of excellent heat resistance.

Further, when a composition including the compound (E) of the present invention is added to the thermoplastic resin, the composition has an effect of improving the heat resistance of a thermoplastic resin and suppressing an increase in the viscosity of a solution to which the composition is added. Therefore, the present composition may be used as an additive to a paint or the like.

[Resin Composition]

The resin composition of the present invention is a resin composition including the above-described high-molecular-weight compound and a thermoplastic resin (first aspect), or a resin composition including the above-described composition and a thermoplastic resin (second aspect).

<Resin Composition Including High-Molecular-Weight Compound and Thermoplastic Resin>

The resin composition of the present invention (first aspect) has excellent heat resistance.

Since the resin composition of the first aspect includes the high-molecular-weight compound of the present invention, the thermal decomposition of the thermoplastic resin is rapidly stopped due to a chain transfer reaction by a thiol group of the high-molecular-weight compound even when the thermoplastic resin starts to be thermally decomposed. In addition, since the thermal decomposition is stopped at an end point with a cleavage of the S—C bond of the thioether structure or the thiourethane structure even when the high-molecular-weight compound starts to be thermally decomposed, the decomposed components remain without volatilization and the effect by the thiol group is sufficiently exerted. In addition, since the boiling point of the high-molecular-weight compound tends to be higher than the molding temperature of the resin composition, the high-molecular-weight compound can be suppressed from volatilizing during molding to cause problems such as foaming in the molded product.

Therefore, a paint using the resin composition of the present invention (first aspect) provides a coating film with high heat resistance. In addition, the viscosity of the paint hardly increases and the paint has excellent handleability, which provides an effect of making it easy to perform painting work.

In the resin composition of the present invention (first aspect), the high-molecular-weight compounds of the present invention may be used alone or in combination of two or more kinds thereof.

Specific examples of the thermoplastic resin include polyamide, polyester, polycarbonate, polyethersulfone, polyphenylene ether, polyphenylene sulfide, polyether ether ketone, polyether ketone, polyimide, polytetrafluoroethylene, polyether, polyolefin, a liquid crystal polymer, polyarylate, polysulfone, polyacrylonitrile styrene, polystyrene, polyacrylonitrile, polymethyl methacrylate (PMMA), polyglycidyl methacrylate (PGMA), and an acrylonitrile-butadiene-styrene copolymer (ABS).

As the thermoplastic resin, an addition-polymerization polymer such as polysulfone, polyacrylonitrile styrene, polystyrene, polyacrylonitrile, polymethyl methacrylate (PMMA), polyglycidyl methacrylate (PGMA), or an acrylonitrile-butadiene-styrene copolymer (ABS) is preferable.

The thermoplastic resins may be used alone or in combination of two or more kinds thereof.

A lower limit value of the mass ratio (high-molecular-weight compound/thermoplastic resin) of the high-molecular-weight compound of the present invention to the thermoplastic resin in the resin composition of the present invention (first aspect) is not particularly limited, but is preferably 0.1/99.9 or more, more preferably 0.5/99.5 or more, still more preferably 1/99 or more, even still more preferably 2/98 or more, and particularly preferably 10/90 or more.

On the other hand, an upper limit value of the mass ratio (high-molecular-weight compound/thermoplastic resin) is not particularly limited, but is preferably 95/5 or less, more preferably 90/10 or less, and still more preferably 80/20.

When the mass ratio (high-molecular-weight compound/thermoplastic resin) is the lower limit value or more, the heat resistance tends to be improved since the resin composition has a sufficient amount of thiol groups necessary for exhibiting an effect of suppressing thermal decomposition.

When the mass ratio (high-molecular-weight compound/thermoplastic resin) is the upper limit value or less, a contribution by the suppression of thermal decomposition for the thermoplastic resin is sufficiently large, whereby the heat resistance tends to be improved.

The resin composition of the present invention (first aspect) may include components other than the high-molecular-weight compound of the present invention and the thermoplastic resin as long as the effects of the present invention are not impaired.

Examples of the other components include additives such as a pigment, an ultraviolet absorber, an adhesion promoter, a release agent, a stabilizer, an antioxidant, a defoaming agent, a plasticizer, and a viscosity modifier.

Known compounds can be used as these additives.

The other components may be used alone or in combination of two or more kinds thereof.

In addition, the content of the other components in the resin composition of the present invention (first aspect) may be appropriately selected according to an intended use, but is preferably 5% by mass or less, more preferably 3% by mass or less, and still more preferably 1% by mass or less, with respect to the total mass of the resin composition of the present invention (first aspect).

A method for producing the resin composition of the present invention (first aspect) is not particularly limited, and examples thereof include a method in which the high-molecular-weight compound of the present invention, a thermoplastic resin, and other components used as necessary are kneaded by a known method.

Since the high-molecular-weight compound of the present invention suppresses an increase in the viscosity of a solution obtained therefrom and has high handleability, it can be easily added to the thermoplastic resin.

<Resin Composition Including Composition and Thermoplastic Resin>

The resin composition of the present invention (second aspect) has excellent heat resistance.

Since the resin composition of the second aspect includes the composition of the present invention, the thermal decomposition of the thermoplastic resin is stopped rapidly due to a chain transfer reaction by a thiol group of the compound (E) even when the thermoplastic resin starts to be thermally decomposed. In addition, since the compound (E) has high thermal decomposition resistance and a high boiling point, it remains without volatilization and sufficiently exerts an effect by the thiol group.

Therefore, a paint using the resin composition of the present invention (second aspect) has high heat resistance of the coating film. In addition, the viscosity of the paint hardly increases and the paint has excellent handleability, which provides an effect of making it easy to perform painting work.

In the resin composition of the present invention (second aspect), the compositions of the present invention may be used alone or in combination of two or more kinds thereof.

The thermoplastic resin is the same as the thermoplastic resin in the resin composition of the present invention (first aspect).

A lower limit value of the mass ratio (composition/thermoplastic resin) of the composition of the present invention to the thermoplastic resin in the resin composition of the present invention (second aspect) is not particularly limited, but is preferably 0.1/99.9 or more, more preferably 0.5/99.5 or more, still more preferably 1/99 or more, even still more preferably 2/98 or more, and particularly preferably 10/90 or more.

On the other hand, an upper limit value of the mass ratio (composition/thermoplastic resin) is not particularly limited, but is preferably 95/5 or less, more preferably 90/10 or less, and still more preferably 80/20 or less.

When the mass ratio (composition/thermoplastic resin) is the lower limit value or more, the resin composition has a sufficient amount of thiol groups necessary for exhibiting an effect of suppressing thermal decomposition, whereby the heat resistance is improved.

When the mass ratio (composition/thermoplastic resin) is the upper limit value or less, a contribution by the suppression of thermal decomposition for the thermoplastic resin is sufficiently large, whereby the heat resistance is improved.

The resin composition of the present invention (second aspect) may include components other than the composition of the present invention and the thermoplastic resin as long as the effects of the present invention are not impaired.

Examples of the other components include additives such as a pigment, an ultraviolet absorber, an adhesion promoter, a release agent, a stabilizer, an antioxidant, a defoaming agent, a plasticizer, and a viscosity modifier.

Known compounds can be used as these additives.

The other components may be used alone or in combination of two or more kinds thereof.

In addition, the content of the other components in the resin composition of the present invention (second aspect) may be appropriately selected according to an intended use, but is preferably 5% by mass or less, more preferably 3% by mass or less, and still more preferably 1% by mass or less, with respect to the total mass of the resin composition of the present invention (second aspect).

A method for producing the resin composition of the present invention (second aspect) is not particularly limited, and examples thereof include a method in which the composition of the present invention, a thermoplastic resin, and other components used as necessary are kneaded by a known method.

Since the composition of the present invention suppresses an increase in the viscosity of a solution obtained therefrom and has high handleability, it can be easily added to the thermoplastic resin.

Furthermore, both of the high-molecular-weight compound of the present invention and the composition of the present invention may be added to the thermoplastic resin to obtain a resin composition. In that case, the total amount of both of the high-molecular-weight compound of the present invention and the composition of the present invention is used as the mass ratio with the resin composition.

[Additive for Lubricating Oil and Lubricating Oil]

The additive for a lubricating oil of the present invention is a high-molecular-weight compound having a plurality of polymer chains linked through a divalent or higher-valent linking group, in which the linking group has a thiol group and at least one of a thioether structure and a thiourethane structure, and a ratio of an absolute weight-average molecular weight to a relative weight-average molecular weight (absolute Mw/relative Mw) of the high-molecular-weight compound is 1.25 or more.

In addition, the lubricating oil of the present invention includes such an additive for a lubricating oil.

The lubricating oil is used for internal combustion engines of vehicles and so-called drive systems such as ATF, MTF, and CVTF, but when the viscosity of the lubricating oil is too high, the operability is deteriorated, and when the viscosity is too low, a surface of the lubricating oil comes into contact due to oil film shortage to easily increase friction or cause wear, ghosting, and the like. Therefore, the lubricating oil is required to have an appropriate viscosity from a low temperature to a high temperature and not to cause a decrease in the viscosity due to a shearing force during use. A viscosity index is an index showing the temperature dependence of a viscosity of the lubricating oil, and the larger the viscosity index, the smaller a fluctuation of the viscosity due to a temperature change.

In the related art, a viscosity index improver used for a lubricating oil tends to cause a deterioration of shear stability when it is intended to enhance an effect of improving the viscosity index of the lubricating oil, whereas the viscosity index improver tends to cause a decrease in the effect of improving the viscosity index when it is intended to enhance the shear stability. Therefore, it was difficult for the viscosity index improver to satisfy both the characteristics.

The additive for a lubricating oil of the present invention imparts a lubricating oil with a viscosity index sufficiently satisfying required performance even with a fluctuation of the temperature, and hardly reduces the shear stability of the lubricating oil. Accordingly, the additive for a lubricating oil is extremely excellent as a viscosity index improver. Further, a lubricating oil including the additive for a lubricating oil of the present invention has a high viscosity index and high shear stability.

The high-molecular-weight compound used in the present invention and a method for producing the same will be described below, but the description above is applied as it is unless otherwise specified.

Examples of the compound (B) include a (meth)acrylic acid, mono(meth)acrylate-based compounds, poly(meth)acrylate-based compounds, monovinyl-based compounds, polyvinyl-based compounds, monoepoxy-based compounds, polyepoxy-based compounds, monoisocyanate-based compounds, and polyisocyanate-based compounds.

Examples of the mono(meth)acrylate-based compounds include alkyl (meth)acrylate, hydroxyethyl (meth)acrylate, hydroxypropyl (meth)acrylate, glycidyl (meth)acrylate, methoxyethyl (meth)acrylate, ethoxyethyl (meth)acrylate, and ethoxyethoxyethyl (meth)acrylate.

Hereinafter, the branched alkyl group shall include a cyclic alkyl group.

Examples of the alkyl (meth)acrylate include a (meth)acrylate compound which has a linear or branched alkyl group having 6 to 30 carbon atoms.

As the (meth)acrylate compound which has a linear or branched alkyl group having 6 to 30 carbon atoms, n-hexyl (meth)acrylate, n-heptyl (meth)acrylate, n-octyl (meth)acrylate, n-nonyl (meth)acrylate, n-decyl (meth)acrylate, n-undecyl (meth)acrylate, n-dodecyl (meth)acrylate, n-tridecyl (meth)acrylate, n-tetradecyl (meth)acrylate, n-pentadecyl (meth)acrylate, n-hexadecyl (meth)acrylate, n-heptadecyl (meth)acrylate, n-octadecyl (meth)acrylate, n-nonadecyl (meth)acrylate, n-eicosyl (meth)acrylate, n-heneicosyl (meth)acrylate, n-docosyl (meth)acrylate, n-tricosyl (meth)acrylate, n-tetracosyl (meth)acrylate, n-pentacosyl (meth)acrylate, n-hexacosyl (meth)acrylate, n-heptacosyl (meth)acrylate, n-octacosyl (meth)acrylate, n-nonacosyl (meth)acrylate, n-triacontyl (meth)acrylate, 1-methyl-n-pentyl (meth)acrylate, 1,2-dimethyl-n-pentyl (meth)acrylate, 1-methyl-n-hexyl (meth)acrylate, isooctyl (meth)acrylate, 2-ethylhexyl (meth)acrylate, 1-ethyl-2,2-dimethyl-n-propyl (meth)acrylate, isononyl (meth)acrylate, 1-methyl-n-nonyl (meth)acrylate, 1-methyl-n-decyl (meth)acrylate, 3,5,5-trimethylhexyl(meth)acrylate, 2,4,6-trimethylheptyl (meth)acrylate, 2-methyl-n-nonyl (meth)acrylate, isodecyl (meth)acrylate, 2-methyl-n-decyl (meth)acrylate, 2-ethyl-n-nonyl (meth)acrylate, isoundecyl (meth)acrylate, isododecyl (meth)acrylate, 2-ethyl-n-decyl (meth)acrylate, 1-ethyl-n-tridecyl (meth)acrylate, 2-decyltetradecyl (meth)acrylate, 2-dodecylhexadecyl (meth)acrylate, or 2-tetradecylhexadecyl (meth)acrylate is preferable since when this compound is used as the chain transfer agent (F) for polymerization, the solubility in a solvent is improved.

Among the (meth)acrylate compounds which have a linear or branched alkyl group having 6 to 30 carbon atoms, n-octyl (meth)acrylate, n-nonyl (meth)acrylate, n-decyl (meth)acrylate, n-undecyl (meth)acrylate, n-dodecyl (meth)acrylate, n-tridecyl (meth)acrylate, n-tetradecyl (meth)acrylate, n-pentadecyl (meth)acrylate, n-hexadecyl (meth)acrylate, n-heptadecyl (meth)acrylate, n-octadecyl (meth)acrylate, n-nonadecyl (meth)acrylate, n-eicosyl (meth)acrylate, n-heneicosyl (meth)acrylate, n-docosyl (meth)acrylate, isooctyl (meth)acrylate, 2-ethylhexyl (meth)acrylate, 1-ethyl-2,2-dimethyl-n-propyl (meth)acrylate, isononyl (meth)acrylate, 1-methyl-n-nonyl (meth)acrylate, 1-methyl-n-decyl (meth)acrylate, 3,5,5-trimethylhexyl (meth)acrylate, 2,4,6-trimethylheptyl (meth)acrylate, 2-methyl-n-nonyl (meth)acrylate, isodecyl (meth)acrylate, 2-methyl-n-decyl (meth)acrylate, 2-ethyl-n-nonyl (meth)acrylate, isoundecyl (meth)acrylate, isododecyl (meth)acrylate, 2-ethyl-n-decyl (meth)acrylate, or 1-ethyl-n-tridecyl (meth)acrylate, which has a linear or branched alkyl group having 8 to 22 carbon atoms, is preferable.

The (meth)acrylate compound which has a linear or branched alkyl group having 22 or less carbon atoms has low crystallinity, high handleability, and high solubility in the polyfunctional thiol compound (A). By using a (meth)acrylate monomer which has a linear or branched alkyl group having 8 or more carbon atoms, the solubility in a solvent when the (meth)acrylate monomer is used as a chain transfer agent (F) for polymerization is improved.

Examples of the poly(meth)acrylate-based compounds include a diester compound obtained by reacting a diol with a (meth)acrylic acid, a polyester compound obtained by reacting a compound having three or more hydroxyl groups per molecule with a (meth)acrylic acid, and a compound obtained by reacting a compound having two or more epoxy groups with a (meth)acrylic acid.

Specific examples of the diester compound obtained by reacting a diol with a (meth)acrylic acid include ethylene glycol di(meth)acrylate, polyethylene glycol di(meth)acrylate, propylene glycol di(meth)acrylate, polypropylene glycol di(meth)acrylate, 1,3-butylene glycol di(meth)acrylate, 1,6-hexanediol di(meth)acrylate, 1,9-nonanediol di(meth)acrylate, 1,10-decanediol di(meth)acrylate, neopentyl glycol di(meth)acrylate, tetraethylene glycol di(meth)acrylate, 2-hydroxy-1,3-di(meth)acryloxypropane, 2,2-bis[4-((meth)acryloxyethoxy)phenyl]propane, 2,2-bis[4-((meth)acryloxy/polyethoxy)phenyl]propane, bis[4-((meth)acryloxy/ethoxy)phenyl]methane, 2-hydroxy-1-(meth)acryloxy-3-(meth)acryloxypropane, and tricyclodecane dimethanol diacrylate.

Specific examples of the polyester compound obtained by reacting a compound having three or more hydroxyl groups per molecule with a (meth)acrylic acid include trimethylolpropane tri(meth)acrylate, tetramethylol tri(meth)acrylate, tetramethylolmethane tetra(meth)acrylate, pentaerythritol tetrakis(meth)acrylate, and dipentaerythritol hexakis(meth)acrylate.

Specific examples of the compound obtained by reacting a compound having two or more epoxy groups with a (meth)acrylic acid include bisphenol A diglycidyl ether and bisphenol F diglycidyl ether.

As the compound (B), a mono- or polyacrylate is preferable from the viewpoint that it has a favorable reactivity with the polyfunctional thiol compound (A), the polyacrylate is more preferable from the viewpoint that it can be reacted with the polyfunctional thiol compound (A) to prepare a high-molecular-weight chain transfer agent (F), and a diacrylate and a triacrylate are still more preferable in order to suppress crosslinking.

These may be used alone or in combination of two or more kinds thereof. For example, the diacrylate or triacrylate, and the monoacrylate may be used in combination.

Examples of the monovinyl-based compounds, the polyvinyl-based compounds, the monoepoxy-based compounds, the polyepoxy-based compounds, the monoisocyanate-based compounds, and the polyisocyanate-based compounds used as the compound (B) include those described above.

As the compound (B), 1,6-hexanediol di(meth)acrylate, 2-ethylhexyl (meth)acrylate, 1,9-nonanediol di(meth)acrylate, 1,10-decanediol di(meth)acrylate, n-nonyl (meth)acrylate, n-decyl (meth)acrylate, n-undecyl (meth)acrylate, n-dodecyl (meth)acrylate, n-tridecyl (meth)acrylate, n-tetradecyl (meth)acrylate, tricyclodecane dimethanol di(meth)acrylate, or the like is preferable. The compounds (B) may be used alone or in combination of two or more kinds thereof.

The high-molecular-weight compound preferably used in the additive for a lubricating oil of the present invention has a structural unit derived from the following radically polymerizable monomer (D) as a polymer chain.

Examples of the radically polymerizable monomer (D) include the (meth)acrylic acid, the mono(meth)acrylate-based compounds, the poly(meth)acrylate-based compounds, the monovinyl-based compounds, and the polyvinyl-based compounds exemplified in the compound (B).

As the radically polymerizable monomer (D), the mono (meth)acrylate-based compounds are preferable, the mono (meth)acrylate compound is more preferable, and a monomethacrylic acid ester compound is the most preferable.

Examples of the mono(meth)acrylate compound include methyl (meth)acrylate, ethyl (meth)acrylate, ethyl (meth)acrylate, n-propyl (meth)acrylate, isopropyl (meth)acrylate, n-butyl (meth)acrylate, isobutyl acrylate, t-butyl (meth)acrylate, n-pentyl (meth)acrylate, neopentyl (meth)acrylate, n-hexyl (meth)acrylate, n-heptyl (meth)acrylate, n-octyl (meth)acrylate, n-nonyl (meth)acrylate, n-decyl (meth)acrylate, n-undecyl (meth)acrylate, n-dodecyl (meth)acrylate, n-tridecyl (meth)acrylate, n-tetradecyl (meth)acrylate, n-pentadecyl (meth)acrylate, n-hexadecyl (meth)acrylate, n-heptadecyl (meth)acrylate, n-octadecyl (meth)acrylate, n-nonadecyl (meth)acrylate, n-eicosyl (meth)acrylate, n-heneicosyl (meth)acrylate, n-docosyl (meth)acrylate, n-tricosyl (meth)acrylate, n-tetracosyl (meth)acrylate, n-pentacosyl (meth)acrylate, n-hexacosyl (meth)acrylate, n-heptacosyl (meth)acrylate, n-octacosyl (meth)acrylate, n-nonacosyl (meth)acrylate, n-triacontyl (meth)acrylate, 1-methyl-n-pentyl (meth)acrylate, 1,2-dimethyl-n-pentyl (meth)acrylate, 1-methyl-n-hexyl (meth)acrylate, isooctyl (meth)acrylate, 2-ethylhexyl (meth)acrylate, 1-ethyl-2,2-dimethyl-n-propyl (meth)acrylate, isononyl (meth)acrylate, 1-methyl-n-nonyl (meth)acrylate, 1-methyl-n-decyl (meth)acrylate, 3,5,5-trimethylhexyl(meth)acrylate, 2,4,6-trimethylheptyl (meth)acrylate, 2-methyl-n-nonyl (meth)acrylate, isodecyl (meth)acrylate, 2-methyl-n-decyl (meth)acrylate, 2-ethyl-n-nonyl (meth)acrylate, isoundecyl (meth)acrylate, isododecyl (meth)acrylate, 2-ethyl-n-decyl (meth)acrylate, 1-ethyl-n-tridecyl (meth)acrylate, 2-decyltetradecyl (meth)acrylate, 2-dodecylhexadecyl (meth)acrylate, and 2-tetradecylhexadecyl (meth)acrylate.

Among the mono(meth)acrylate compounds, n-hexyl (meth)acrylate, n-heptyl (meth)acrylate, n-octyl (meth)acrylate, n-nonyl (meth)acrylate, n-decyl (meth)acrylate, n-undecyl (meth)acrylate, n-dodecyl (meth)acrylate, n-tridecyl (meth)acrylate, n-tetradecyl (meth)acrylate, n-pentadecyl (meth)acrylate, n-hexadecyl (meth)acrylate, n-heptadecyl (meth)acrylate, n-octadecyl (meth)acrylate, n-nonadecyl (meth)acrylate, n-eicosyl (meth)acrylate, n-heneicosyl (meth)acrylate, n-docosyl (meth)acrylate, isooctyl (meth)acrylate, 2-ethylhexyl (meth)acrylate, 1-ethyl-2,2-dimethyl-n-propyl (meth)acrylate, isononyl (meth)acrylate, 1-methyl-n-nonyl (meth)acrylate, 1-methyl-n-decyl (meth)acrylate, 3,5,5-trimethylhexyl(meth)acrylate, 2,4,6-trimethylheptyl (meth)acrylate, 2-methyl-n-nonyl (meth)acrylate, isodecyl (meth)acrylate, 2-methyl-n-decyl (meth)acrylate, 2-ethyl-n-nonyl (meth)acrylate, isoundecyl (meth)acrylate, isododecyl (meth)acrylate, 2-ethyl-n-decyl (meth)acrylate, or 1-ethyl-n-tridecyl (meth)acrylate, which has a linear or branched alkyl group having 6 to 22 carbon atoms, is preferable.

As the mono(meth)acrylate compound, the (meth)acrylate monomer which has a linear or branched alkyl group having 6 to 22 carbon atoms as described above is preferably used, a (meth)acrylate compound which has a linear or branched alkyl group having 8 to 15 carbon atoms is more preferable, and a (meth)acrylate compound which has a linear or branched alkyl group having 9 to 15 carbon atoms is still more preferable.

When the number of carbon atoms is the upper limit value or less, the crystallinity is low and the handleability is high.

When the number of carbon atoms is the lower limit value or more, the obtained high-molecular-weight compound has high solubility in a lubricating oil, and is more suitable as an additive for a lubricating oil.

The content of the (meth)acrylate compound which has an alkyl group having the number of carbon atoms in the range is preferably 10% to 100% by mole, more preferably 15% to 80% by mole, and still more preferably 20% to 60% by mole, with respect to 100% by mole of the total amount of radically polymerizable monomers (D).

When the content of the (meth)acrylate compound which has an alkyl group having the number of carbon atoms in the range is the lower limit value of the range or more, the solubility of a high-molecular-weight compound thus obtained in a lubricating oil is maintained, and when the content is the upper limit value of the range or less, an effect of improving the viscosity index of a high-molecular-weight compound thus obtained is further enhanced.

Furthermore, it is preferable to use a (meth)acrylate compound which has an alkyl group having the number of carbon atoms in the range and a (meth)acrylate compound which has a linear alkyl group having 5 or less carbon atoms in combination as the radically polymerizable monomer (D). Thus, the steric hindrance at the time of a reaction with the chain transfer agent (F) is appropriately reduced and the reaction rate of the chain transfer agent (F) with a thiol group is increased. Therefore, a high-molecular-weight compound thus obtained has an increased degree of branching and improved shear stability. In addition, the chain transfer agent (F) is easily dissolved in the monomer (D), and thus, a uniform polymerization system is created, which enhances the reactivity.

The content of the (meth)acrylate compound which has a linear alkyl group having 5 or less carbon atoms in 100% by mole of the total amount of radically polymerizable monomers (D) is preferably 0% to 90% by mole, more preferably 20% to 85% by mole, and still more preferably 40% to 80% by mole. When the content is the lower limit value of the range or more, the shear stability of a high-molecular-weight compound thus obtained is further enhanced, and when the content is the upper limit value of the range or less, the solubility of a high-molecular-weight compound thus obtained in a lubricating oil is further enhanced.

Examples of the (meth)acrylate compound which has a linear alkyl group having 5 or less carbon atoms include methyl methacrylate, ethyl methacrylate, n-propyl methacrylate, n-butyl methacrylate, and n-pentyl methacrylate. The (meth)acrylate compound is preferably a (meth)acrylate compound which has a linear alkyl group having 4 or less carbon atoms, more preferably methyl methacrylate or n-butyl methacrylate, and most preferably n-butyl methacrylate.

Structural units derived from the radically polymerizable monomers (D) that form the polymer chain may be of one or more kinds.

Furthermore, a structural unit other than the structural unit derived from the (meth)acrylate compound having a linear or branched alkyl group may be included. The content thereof is preferably 5% by mass or less, more preferably 3% by mass or less, and most preferably 1% by mass or less.

The high-molecular-weight compound of the present invention can be obtained, for example, by radically polymerizing the radically polymerizable monomers (D) using a chain transfer agent (F).

The amount of chain transfer agent (F) to be used is preferably 0.1 to 20 parts by mass, more preferably 0.2 to 15 parts by mass, and most preferably 0.3 to 10 parts by mass, with respect to 100 parts by mass of the total amount of radically polymerizable monomers (D). When the amount is the lower limit value of the range or more, the degree of branching of the high-molecular-weight compound of the present invention is easily enhanced, and when the amount is the upper limit value of the range or less, an effect of improving the viscosity index of a high-molecular-weight compound thus obtained is easily enhanced.

The form of radical polymerization is not particularly limited, and examples thereof include methods of solution polymerization, bulk polymerization, suspension polymerization, emulsion polymerization, reversed phase suspension polymerization, reversed phase emulsion polymerization, soap-free polymerization, and precipitation polymerization.

Among the radical polymerizations, the solution polymerization is preferable from the viewpoint of simplicity. Examples of the polymerization solvent include aromatic hydrocarbon-based solvents (toluene, ethylbenzene, xylene, and the like), aliphatic hydrocarbon-based solvents (pentane, hexane, heptane, octane, cyclohexane, and the like), ketone-based solvents (acetone, methyl isobutyl ketone, methyl ethyl ketone, and the like), ester-based solvents (butyl acetate and the like), and alcohol-based solvents (methanol, ethanol, and the like). The polymerization solvents may be of one or more kinds.

The polymerization solvent is preferably the hydrocarbon-based solvent. As the hydrocarbon-based solvent, a liquid hydrocarbon is more preferably used. As the liquid hydrocarbon, a hydrocarbon that is liquid at 25° C., among paraffin, cycloparaffin, and aromatic hydrocarbons, is more preferably used. A liquid hydrocarbon used as a base oil in a final product, which has a density (vibration type) of less than 1 g/cm$^3$ at 15° C. and a viscosity of 5.0 cP or more at 25° C., among paraffin, cycloparaffin and aromatic hydrocarbons, is still more preferable. Examples thereof include lubricating base oils such as vegetable oils, mineral oils, and synthetic oils such as PAO. Among these, paraffin, cycloparaffin, or a mixture thereof is preferable from the viewpoints of viscosity and kinematic viscosity.

In addition, the polymerization solvent preferably has a boiling point of 100° C. or higher, and examples thereof include paraffin, cycloparaffin, toluene, and a mixture thereof.

In particular, it is preferable to perform polymerization in a liquid hydrocarbon used in a final product since troubles of precipitating the high-molecular-weight compound of the present invention, obtained by the polymerization, in a poor solvent, drying the solvent, or dissolving the resultant in the liquid hydrocarbon can be saved.

The amount of the polymerization solvent to be used is preferably 50 to 1,000 parts by mass, and more preferably 100 to 500 parts by mass, with respect to 100 parts by mass of the total amount of radically polymerizable monomers (D). When the amount is the lower limit value of the range or more, the polymerization rate of the high-molecular-weight compound obtained after the polymerization easily increases, and when the amount is the upper limit value of the range or less, an excessive increase in the viscosity can be prevented, and handleability and process passability are favorable.

Examples of the radical polymerization initiator include peroxides such as dibenzoyl peroxide and tert-butyl permalate, and azo-based compounds such as 2,2'-azobisisobutyronitrile and azobisisovaleronitrile. The azo-based compounds are preferable since they do not easily react with a thiol group in the chain transfer agent (F). The radical polymerization initiators may be of one or more kinds.

The amount of radical polymerization initiator to be used is preferably 0.0001 to 10 parts by mass, more preferably 0.001 to 5 parts by mass, and still more preferably 0.01 to 1 part by mass, with respect to 100 parts by mass of the total amount of radically polymerizable monomers (D). When the amount is the lower limit value of the range or more, the polymerization rate of a high-molecular-weight compound thus obtained is sufficiently high, and when the amount is the upper limit value of the range or less, it is less likely to be adversely affected by impurities.

A polymerization temperature for the radical polymerization can be appropriately set, and is preferably –100° C. to 250° C., more preferably 0° C. to 150° C., and still more preferably 30° C. to 100° C., for example, from the viewpoint that it is suitable as a temperature range of the radical polymerization initiator to be used.

A polymerization time for the radical polymerization can be appropriately set, and is, for example, preferably 0.5 to 48 hours, more preferably 1 to 24 hours, and most preferably 2 to 12 hours. When the polymerization is performed for a polymerization time which is the lower limit value or more, a conversion rate can be increased, and when the polymerization is performed for a polymerization time which is the upper limit value or less, power and cost required for the polymerization can be decreased.

A lower limit value of a ratio (absolute Mw/relative Mw) of the absolute weight-average molecular weight (hereinafter also referred to as "absolute Mw") to the relative weight-average molecular weight (hereinafter also referred to as "relative Mw") of the high-molecular-weight compound of the present invention is 1.25 or more, preferably 1.27 or more, more preferably 1.29 or more, and still more preferably 1.30 or more.

When the ratio (absolute Mw/relative Mw) is the lower limit value or more, the high-molecular-weight compound has sufficient branches, and when the high-molecular-weight compound is used as an additive for a lubricating oil, the shear stability of the lubricating oil is further enhanced.

On the other hand, an upper limit value of the ratio (absolute Mw/relative Mw) is not particularly limited, but is usually 3.00 or less, preferably 2.80 or less, more preferably 2.50 or less, and still more preferably 2.15 or less.

When the ratio (absolute Mw/relative Mw) is the upper limit value or less, an effect of improving the viscosity index of a high-molecular-weight compound thus obtained as an additive for a lubricating oil is further enhanced.

A lower limit value of the relative Mw of the high-molecular-weight compound of the present invention is not particularly limited, but is preferably 5,000 or more, more preferably 10,000 or more, still more preferably 15,000 or more, and even still more preferably 17,000 or more.

On the other hand, an upper limit value of the relative Mw of the high-molecular-weight compound of the present invention is not particularly limited, but is preferably 350,000 or less, more preferably 200,000 or less, still more preferably 50,000 or less, and even still more preferably 45,000 or less.

When the relative Mw of the high-molecular-weight compound of the present invention is the lower limit value or more, branches are easily generated and an effect of improving the viscosity index is excellent.

When the relative Mw of the high-molecular-weight compound of the present invention is the upper limit value or less, an effect of improving the viscosity index is excellent, and the shear stability is also excellent at the same time.

A lower limit value of the absolute Mw of the high-molecular-weight compound of the present invention is not particularly limited, but is preferably 6,250 or more, more preferably 12,500 or more, still more preferably 18,750 or more, and even still more preferably 21,250 or more.

On the other hand, an upper limit value of the absolute Mw of the high-molecular-weight compound of the present invention is not particularly limited, but is preferably 1,050,000 or less, more preferably 600,000 or less, still more preferably 150,000 or less, and even still more preferably 135,000 or less.

When the absolute Mw of the high-molecular-weight compound of the present invention is the lower limit value or more, branches are easily generated and an effect of improving the viscosity index is also excellent.

When the absolute Mw of the high-molecular-weight compound of the present invention is the upper limit value or less, an effect of improving the viscosity index is excellent, and the shear stability is also excellent at the same time.

A range of the relative Mw of the chain transfer agent (F) is not particularly limited, but is preferably 500 to 50,000, more preferably 1,000 to 40,000, and still more preferably 2,000 to 25,000.

When the relative Mw of the chain transfer agent (F) is the lower limit value of the range or more, the high-molecular-weight compound of the present invention can be easily obtained, and when the relative Mw is the upper limit value of the range or less, difficulty in handleability due to thickening is easily solved.

The high-molecular-weight compound of the present invention is preferably one with which a liquid hydrocarbon solution is obtained. After polymerizing the high-molecular-weight compound by solution polymerization, the solvent may be dried and then the resultant may be dissolved in the liquid hydrocarbon as described above, but it is preferable to directly obtain a liquid hydrocarbon solution of the high-molecular-weight compound by performing solution polymerization in the liquid hydrocarbon.

It is more preferable to obtain a hydrocarbon solution of the high-molecular-weight compound by reacting the thiol group-containing compound (A) with the compound (B) containing a functional group that reacts with a thiol group in a hydrocarbon solvent to synthesize a chain transfer agent (F), and then performing radical polymerization using the chain transfer agent (F). Alternatively, a hydrocarbon solution of the high-molecular-weight compound is obtained by reacting the thiol group-containing compound (A) with the functional group-containing compound (B) that reacts with a thiol group to synthesize a chain transfer agent (F), and then dissolving the chain transfer agent (F) in radically polymerizable monomers (D) to perform radical polymerization in a hydrocarbon solvent.

The concentration of the high-molecular-weight compound in the liquid hydrocarbon solution can be appropriately adjusted according to a use, but is preferably 5% to 60% by mass, more preferably 10% to 50% by mass, and most preferably 15% to 40% by mass. When the concentration is the lower limit value or more, the transportation cost is suppressed, and when the concentration is the upper limit value or less, the high-molecular-weight compound is less likely to precipitate due to a temperature change.

The high-molecular-weight compound of the present invention can be used as an additive for a lubricating oil. The additive for a lubricating oil can play various roles as a viscosity index improver, a friction-reducing agent, a pour point depressant, a preservative, or the like. The high-molecular-weight compound of the present invention can be effectively used as the viscosity index improver, the friction-reducing agent, or the pour point depressant among those. In particular, the high-molecular-weight compound exhibits its performance as the viscosity index improver. Furthermore, the high-molecular-weight compound can also have shear stability. In addition, the high-molecular-weight compound can be effectively used in combination with other additives.

The lubricating oil is a base oil to which a viscosity index improver, a friction-reducing agent, a pour point depressant, a preservative, a cleaning agent, a defoaming agent or the like has been added. The base oil is a liquid hydrocarbon, examples thereof include vegetable oils, mineral oils refined from crude oils, and chemically synthesized synthetic oils such as PAO, and the base oil are selected therefrom according to a purpose.

The additive for a lubricating oil using the high-molecular-weight compound of the present invention can be used without particular limitation for various lubricating oils such as an internal combustion engine lubricating oil, a drive system lubricating oil, and a hydraulic oil, as described above. However, the additive for a lubricating oil is particularly preferably used for the drive system lubricating oil since it has both of an effect of improving viscosity index, and high shear stability.

The lubricating oil may contain various additives in addition to the high-molecular-weight compound of the present invention. Examples of the additive include cleaning agents such as basic, hyperbasic, or neutral metal salts, dispersants such as imides of succinate, antioxidants such as hindered phenols, friction and abrasion modifiers such as molybdenum-based and zinc-based compounds, extreme pressure agents such as sulfur-based compounds, defoaming agents such as silicon oils and fatty acid esters, anti-emulsifiers such as quaternary ammonium salts, and corrosion inhibitors such as nitrogen atom-containing compounds.

The content of the high-molecular-weight compound of the present invention in the lubricating oil is preferably 0.01% to 30% by mass, more preferably 0.1% to 15% by mass, and most preferably 0.5% to 10% by mass when the total mass of the lubricating oil is taken as 100% by mass. When the content is the lower limit value or more, the viscosity index of the lubricating oil is improved, and when the content is the upper limit value or less, precipitation due to a temperature change is easily suppressed.

EXAMPLES

Hereinafter, the present invention will be specifically described with reference to Examples, but is not limited to the following description.

[Materials]

The abbreviations of the raw materials used in the present Examples are shown below.

<Polyfunctional Thiol Compound (A)>

PEMP: Pentaerythritol tetrakis(3-mercaptopropionate) (manufactured by SC Organic Chemical Co., Ltd.).

EGMP: Tetraethylene glycol bis(3-mercaptopropionate) (manufactured by SC Organic Chemical Co., Ltd.).

PEMA: Pentaerythritol tetrakis(2-mercaptoacetate) (manufactured by Tokyo Chemical Industry Co., Ltd.).

DPMP: Dipentaerythritol hexakis(3-mercaptopropionate) (manufactured by SC Organic Chemical Co., Ltd.).

<Compound (B)>

EHA: 2-Ethylhexyl acrylate (manufactured by Mitsubishi Chemical Corporation).

C6DA: 1,6-Hexanediol diacrylate (manufactured by Mitsubishi Chemical Corporation).

TMHDMI: Trimethyl hexamethylene diisocyanate (manufactured by Tokyo Chemical Industry Co., Ltd.).

TMPTA: Trimethylolpropane triacrylate (manufactured by Tokyo Chemical Industry Co., Ltd.).

NPGE: Neopentyl glycol diglycidyl ether (manufactured by Tokyo Chemical Industry Co., Ltd.).

LA: A mixture of n-dodecyl acrylate and n-tetradecyl acrylate (LA1214, manufactured by BASF).

A-DCP: Tricyclodecane dimethanol diacrylate (Shin Nakamura Chemical Industry Co., Ltd.).

A-DOD-N: 1,10-Decanediol diacrylate (Shin Nakamura Chemical Industry Co., Ltd.).

<Catalyst (C)>

TPP: Triphenylphosphine (manufactured by Tokyo Chemical Industry Co., Ltd.).

CHDP: Cyclohexyldiphenylphosphine (manufactured by Tokyo Chemical Industry Co., Ltd.).

(Radically Polymerizable Monomer (D))

MMA: Methyl methacrylate (Acryester M)

BMA: n-Butyl methacrylate (Acryester B)

EHMA: 2-Ethylhexyl methacrylate (Acryester EH)

LMA: Lauryl methacrylate (Acryester L, Dodecyl methacrylate)

TDMA: Tridecyl methacrylate (Acryester TD)

(All manufactured by Mitsubishi Chemical Corporation)

<Thermoplastic Resin>

VHK: Bead type polymethyl methacrylate (PMMA) (trade name "DIANAL BR-80", manufactured by Mitsubishi Chemical Corporation).

VH: Pellet type PMMA (trade name "ACRYPET VH", manufactured by Mitsubishi Chemical Corporation).

PGMA: Polyglycidyl methacrylate (trade name "METABLEN P1901", manufactured by Mitsubishi Chemical Corporation).

PMMA-SH: Thiol Terminated Poly(methyl methacrylate) (manufactured by Polymer Source, Inc.).

[Measurement Method and Evaluation Method]

<Relative Weight-Average Molecular Weight (Relative Mw)>

The relative Mw of the high-molecular-weight compound was measured under the following conditions, using gel permeation chromatography (GPC). Thereafter, the relative Mw was calculated using a calibration curve created with polymethyl methacrylate (four kinds with Mp (peak molecular weight)=141,500, 55,600, 11,100 and 1,590) manufactured by Polymer Laboratories Ltd.

Device: HLC-8220 (manufactured by Tosoh Corporation).

Column: TSK GUARD COLUMN SUPER H-H (4.6×35 mm, manufactured by Tosoh Corporation) and two TSK-GEL SUPER HM-H (6.0×150 mm, manufactured by Tosoh Corporation) are connected in series.

Eluent: Tetrahydrofuran.

Measurement temperature: 40° C.

Flow rate: 0.6 mL/min.

<Absolute Weight-Average Molecular Weight (Absolute Mw)>

The absolute Mw of the high-molecular-weight compound was measured under the following conditions, using gel permeation chromatography (GPCmax manufactured by Viscotek Corporation) and a light-scattering detector. Thereafter, the absolute molecular weight and the intrinsic viscosity at each elution position were calculated using a software (OmniSEC) attached to the device, and the absolute Mw was determined.

Column: One TSKgel guardcolumn HXL-H (6.0×40 mm, manufactured by Tosoh Corporation), two TSKgel GMHXL (7.8×300 mm, manufactured by Tosoh Corporation), and one TSKgel G3000 HXL (7.8×300 mm), manufactured by Tosoh Corporation) are connected in series.

Eluent: Tetrahydrofuran.

Column and detector temperature: 40° C.

Flow rate: 1.0 mL/min.

Detector: TDA302 (manufactured by Viscotek Corporation).

Sample concentration: 2 mg/mL (a polymer was dissolved in tetrahydrofuran).

Injection volume: 150 μL.

Standard for device calibration: Polystyrene (manufactured by Viscotek Corporation, molecular weight 105,000).

<Evaluation of Heat Resistance (ΔTd5)>

A high-molecular-weight compound was added to a thermoplastic resin and melt-kneaded to prepare a resin composition. Unless otherwise specified, the mass ratio was as follows: high-molecular-weight compound:thermoplastic resin=10:90. This resin composition was subjected to thermogravimetric analysis, and the obtained 5%-by-weight reduction temperature (Td5) was defined as the "measured value of Td5 of the resin composition". On the other hand, each of the high-molecular-weight compound and the resin was subjected to thermogravimetric analysis, and the "calculated value of Td5 of the resin composition" was obtained by the following procedures (1) to (3), using those values. The value obtained by subtracting the "calculated value of Td5 of the resin composition" from the "measured value of Td5 of the resin composition" was defined as ΔTd5. With ΔTd5>0, it can be said that the heat resistance is improved.

(1) The high-molecular-weight compound was subjected to thermogravimetric analysis, a weight reduction rate with respect to each temperature was obtained, and a weight reduction rate curve of the high-molecular-weight compound was thus obtained.

(2) The thermoplastic resin was subjected to thermogravimetric analysis, a weight reduction rate with respect to each temperature was obtained, and a weight reduction rate curve of the thermoplastic resin was thus obtained.

(3) A value obtained by dividing the weight reduction rate of the high-molecular-weight compound and the thermoplastic resin at each temperature by the above-described mass ratio was defined as a weight reduction rate of the resin composition, and a weight reduction rate curve was thus obtained. From this, a temperature at which the weight reduction rate was 5% was defined as a "calculated value of Td5 of the resin composition".

The "measured value of Td5 of the resin composition" was determined by subjecting the resin composition to thermogravimetric analysis at the time of a temperature rise using a thermogravimetric and differential thermal simultaneous measuring device, and tracking a weight reduction. The device and the measurement conditions are shown below.

Device: TG/DTA6300 (manufactured by SII Nanotechnology Inc.).

Measurement conditions: Nitrogen air flow 200 mL/min, 30° C. to 500° C., heating rate 10° C./min.

In addition, when a composition including the compound (E) instead of the high-molecular-weight compound was added to a thermoplastic resin, evaluation of the heat resistance (ΔTd5) was performed in the same manner.

<Kinematic Viscosity, Viscosity Index (VI), and Shear Stability Index (SSI)>

A kinematic viscosity at 40° C. (KV40) and a kinematic viscosity at 100° C. (KV100) were measured in accordance with JIS-K2283. The measurements were performed at a concentration of 10% by mass, using YUBASE2 (manufactured by SK Lubricants Co., Ltd., KV40=9.181 mm$^2$/s, density (vibration type) 15° C.=0.8354 g/cm$^3$) as a base oil.

Next, a viscosity index (VI) was calculated according to the method of JIS-K2283-1993, using the obtained kinematic viscosity.

In addition, a CEC-L45-99-based KRL 20 h test was performed with a KRL shear stability tester, kinematic viscosities (KV40 and KV100) before and after the test were measured, and the shear stability index (SSI) was calculated from the following formula. The SSI which is closer to 0 is more preferable.

SSI=(KV100 of pre-test sample−KV100 of post-test sample)/(KV100 of pre-test sample−KV100 of hydrocarbon of base liquid)×100

Production Example 1

To 10 g of PEMP, which is a polyfunctional thiol compound (A), 0.1 g of finely crushed TPP as a catalyst (C) was added, and the mixture was heated to 80° C. with stirring until the mixture was uniform, thereby completely dissolving the components. To 7.33 g of the obtained mixture, 2.26 g of C6DA as a compound (B) was added, and the mixture was stirred at room temperature (25° C.) at a molar ratio of PEMP to C6DA of 1.5:1.0 to obtain a chain transfer agent (F-1).

Production Example 2

A chain transfer agent (F-2) was produced in the same manner as in Production Example 1, except that the molar ratio of PEMP to C6DA was 2.0:1.0.

Production Example 3

A chain transfer agent (F-3) was produced in the same manner as in Production Example 1, except that the molar ratio of PEMP to C6DA was 2.5:1.0.

Production Example 4

A chain transfer agent (F-4) was produced in the same manner as in Production Example 1, except that C6DA and EHA were used as the compound (B) and the molar ratio of PEMP:C6DA:EHA was 1.5:1.0:1.0.

Production Example 5

A chain transfer agent (F-5) was produced in the same manner as in Production Example 1, except that C6DA and EHA were used as the compound (B) and the molar ratio of PEMP:C6DA:EHA was 1.5:1.0:0.5.

Production Example 6

A chain transfer agent (F-6) was produced in the same manner as in Production Example 1, except that TMHDMI and EHA were used as the compound (B) and the molar ratio of PEMP:TMHDMI:EHA was 2.0:1.0:1.0.

Example 1

1. Production and Measurement of High-Molecular-Weight Compound 100 parts by mass of methyl methacrylate (MMA) as a radically polymerizable monomer (D), 6.0 parts by mass of the chain transfer agent (F-1) obtained in Production Example 1, and 0.3 parts by mass of 2,2'-azobisbutyronitrile (AIBN) as a polymerization initiator were added into a 250 mL four-necked separable flask equipped with a stirrer, a nitrogen inlet pipe, a thermometer, and a condenser, toluene as a solvent was further added thereto such that the gram equivalent with respect to the monomer components was 1.0, and the reaction mixture was heated to 80° C. with stirring under a nitrogen atmosphere. After heating and stirring for 5 hours, the mixture was reprecipitated using hexane as a poor solvent to obtain a high-molecular-weight compound.

The solution viscosity of a solution of the high-molecular-weight compound thus obtained in butyl acetate was measured. That is, the high-molecular-weight compound was dissolved in butyl acetate to adjust the concentration of solid contents to 40% by mass. The viscosity of this solution was measured at room temperature (25° C.) using an E-type viscometer.

2. Production and Measurement of Resin Composition

The obtained high-molecular-weight compound and an acrylic resin (VHK) were mixed so that the high-molecularweight compound/acrylic resin (VHK) (mass ratio)=10/90, and melt-kneaded to prepare a resin composition. The 5%-by-weight reduction temperature of this resin composition was measured to determine ΔTd5, and the effect of improving the heat resistance of the high-molecular-weight compound was evaluated.

The measurement results are shown in Table 1.

Examples 2 to 6

A high-molecular-weight compound and a resin composition were produced in the same manner as in Example 1, except that the type and the amount of chain transfer agent to be used were changed as shown in Table 1.

The solution viscosity of the high-molecular-weight compound and the ΔTd5 of the resin composition were measured.

The measurement results are shown in Table 1.

Example 7

A high-molecular-weight compound and a resin composition were produced in the same manner as in Example 1, except that the thermoplastic resin to be mixed with the high-molecular-weight compound was changed to an acrylic resin VH.

The solution viscosity of the high-molecular-weight compound and the ΔTd5 of the resin composition were measured.

The measurement results are shown in Table 1.

Example 8

A high-molecular-weight compound and a resin composition were produced in the same manner as in Example 1, except that the thermoplastic resin to be mixed with the high-molecular-weight compound was changed to polyglycidyl methacrylate (PGMA).

The solution viscosity of the high-molecular-weight compound and the ΔTd5 of the resin composition were measured.

The measurement results are shown in Table 1.

Example 9

A high-molecular-weight compound and a resin composition were produced in the same manner as in Example 1, except that the type and the amount of chain transfer agent to be used were changed as shown in Table 1.

The solution viscosity of the high-molecular-weight compound and the ΔTd5 of the resin composition were measured.

The measurement results are shown in Table 1.

Comparative Example 1

A high-molecular-weight compound and a resin composition were produced in the same manner as in Example 1, except that the type and the amount of chain transfer agent to be used were changed as shown in Table 1.

The solution viscosity of the high-molecular-weight compound and the ΔTd5 of the resin composition were measured.

The measurement results are shown in Table 1.

Comparative Example 2

A compound (X-1) having a thioether structure but not having a thiol group was produced in the same manner as in Example 1, except that 3.6 parts by mass of stearyl-3-mercaptopropionate (STMP, manufactured by SC Organic Chemical Co., Ltd.) was used instead of the chain transfer agent (F-1).

The obtained compound (X-1) and the acrylic resin (VH), which is a thermoplastic resin, were mixed so that compound (X-1)/acrylic resin (VH) (mass ratio) was 10/90, and stirred at room temperature (25° C.) to prepare a resin composition.

The ΔTd5 of the resin composition was measured.

The measurement results are shown in Table 1.

Comparative Example 3

A resin composition was prepared in the same manner as in Comparative Example 2, except that PMMA-SH was used as the compound (X-2) having a thiol group but not having a thioether structure and a thiourethane structure.

The ΔTd5 of the resin composition was measured.

The measurement results are shown in Table 1.

TABLE 1

| | | | Example | | | | | | | | | Comparative Example | | |
|---|---|---|---|---|---|---|---|---|---|---|---|---|---|---|
| | | | 1 | 2 | 3 | 4 | 5 | 6 | 7 | 8 | 9 | 1 | 2 | 3 |
| MMA [parts by mass] | | | 100 | 100 | 100 | 100 | 100 | 100 | 100 | 100 | 100 | 100 | 100 | 100 |
| Chain transfer agent [parts by mass] | F-1 | | 6 | — | — | — | — | — | 6 | 6 | 4.8 | — | — | — |
| | F-2 | | — | 1 | — | — | — | — | — | — | — | — | — | — |
| | F-3 | | — | — | 1 | — | — | — | — | — | — | — | — | — |
| | F-4 | | — | — | — | 4 | — | — | — | — | — | — | — | — |
| | F-5 | | — | — | — | — | 7 | — | — | — | — | — | — | — |
| | F-6 | | — | — | — | — | — | 3 | — | — | — | — | — | — |
| | PEMP | | — | — | — | — | — | — | — | — | — | 0.12 | — | — |
| | STMP | | — | — | — | — | — | — | — | — | — | — | 3.6 | — |
| Relative Mw (×10³) | | | 45 | 70 | 58 | 60 | 32 | 24 | 45 | 45 | 45 | 70 | 21 | 15 |
| Absolute Mw/relative Mw | | | 1.84 | 1.29 | 1.29 | 1.53 | 1.29 | 1.31 | 1.84 | 1.84 | 2.2 | 1.20 | — | — |
| Solution viscosity [Pa·s] | | | 2.0 | 33.0 | 33.8 | 0.14 | 0.04 | 3.9 | 2.0 | 2.0 | 1.3 | 74.7 | — | — |
| Thermoplastic resin | | | VHK | VHK | VHK | VHK | VHK | VHK | VH | PGMA | VHK | VHK | VH | VH |
| ΔTd5 [° C.] | | | 16.1 | 0.5 | 3.6 | 6.2 | 9.5 | 4.0 | 3.5 | 2.6 | −0.9 | 11.9 | −2.8 | −21.8 |

As shown in Table 1, the high-molecular-weight compound of Examples 1 to 8 enabled the solution including the high-molecular-weight compounds to have a low viscosity and excellent handleability, and when the high-molecular-weight compound was added to the thermoplastic resin, the ΔTd5 was high and the heat resistance was excellent. The high-molecular-weight compound of Example 9 had a low solution viscosity and favorable handleability.

On the other hand, the high-molecular-weight compound of Comparative Example 1 enabled the solution including the high-molecular-weight compound to have a high viscosity and poor handleability. When the high-molecular-weight compound of Comparative Examples 2 and 3 was added to a thermoplastic resin, the ΔTd5 was 0 or less, and an effect of improving the heat resistance was not observed.

In addition, in Examples 1 to 8, when the 5%-by-weight reduction temperature was measured, no odor was generated during heating.

From the above, it was confirmed that the high-molecular-weight compound according to the present invention exhibits excellent properties.

Example 2-1

To 10 g of PEMP, as a polyfunctional thiol compound (A), 0.1 g of finely crushed TPP as a catalyst (C) was added, and the mixture was heated to 80° C. with stirring until the mixture was uniform, thereby completely dissolving the components. To 7.33 g of the obtained mixture, 2.26 g of C6DA as a compound (B) was added, and the mixture was stirred at room temperature (25° C.) to obtain a composition (E-1).

Example 2-2

A composition (E-2) was obtained by performing a reaction in the same manner as in Example 1, except that 1.13 g of C6DA was added to 4.89 g of a mixture of PEMP and TPP.

Example 2-3

A composition (E-3) was obtained by performing a reaction in the same manner as in Example 1, except that 1.13 g of C6DA was added to 6.11 g of a mixture of PEMP and TPP.

Example 2-4

A composition (E-4) was obtained by performing a reaction in the same manner as in Example 1, except that 1.13 g of C6DA was added to 7.33 g of a mixture of PEMP and TPP.

Example 2-5

A composition (E-5) was obtained by performing a reaction in the same manner as in Example 1, except that 1.13 g of C6DA was added to 9.77 g of a mixture of PEMP and TPP.

Example 2-6

A composition (E-6) was obtained by performing a reaction in the same manner as in Example 1, except that DPMP was used instead of PEMP as a polyfunctional thiol compound (A), and 1.13 g of C6DA was added to 7.83 g of a mixture obtained by mixing DPMP and TPP at DPMP/TPP (mass ratio)=10/0.1.

Example 2-7

A composition (E-7) was obtained by performing a reaction in the same manner as in Example 1, except that DPMP was used instead of PEMP as a polyfunctional thiol compound (A), and 1.13 g of C6DA was added to 9.00 g of a mixture obtained by mixing DPMP and TPP at DPMP/TPP (mass ratio)=10/0.1.

Example 2-8

A composition (E-8) was obtained by performing a reaction in the same manner as in Example 1, except that CHDP was used instead of TPP as a compound (B) having a reactive group that reacts with a thiol group, and 0.87 g of NPGE and 0.74 g of EHA were added to 3.91 g of a mixture obtained by mixing PEMP and CHDP at PEMP/CHDP (mass ratio)=20/0.1.

Example 2-9

A composition (E-9) was obtained by performing a reaction in the same manner as in Example 1, except that CHDP was used instead of TPP as a compound (B) having a reactive group that reacts with a thiol group, and 0.84 g of TMHDMI and 0.74 g of EHA were added to 3.91 g of a mixture obtained by mixing PEMP and CHDP at PEMP/CHDP (mass ratio)=20/0.1.

Example 2-10

A composition (E-10) was obtained by performing a reaction in the same manner as in Example 1, except that CHDP was used instead of TPP as a compound (B) having a reactive group that reacts with a thiol group, and 0.91 g of C6DA and 0.74 g of EHA were added to 3.91 g of a mixture obtained by mixing PEMP and CHDP at PEMP/CHDP (mass ratio)=20/0.1.

Example 2-11

A composition (E-11) was obtained by performing a reaction in the same manner as in Example 1, except that CHDP was used instead of TPP as a compound (B) having a reactive group that reacts with a thiol group, and 1.13 g of C6DA and 0.92 g of EHA were added to 3.66 g of a mixture obtained by mixing PEMP and CHDP at PEMP/CHDP (mass ratio)=20/0.1.

Example 2-12

A composition (E-12) was obtained by performing a reaction in the same manner as in Example 1, except that CHDP was used instead of TPP as a compound (B) having a reactive group that reacts with a thiol group, and 1.13 g of C6DA and 0.46 g of EHA were added to 3.91 g of a mixture obtained by mixing PEMP and CHDP at PEMP/CHDP (mass ratio)=20/0.1.

Example 2-13

A reaction was performed in the same manner as in Example 1, except that EGMP was used instead of PEMP as the polyfunctional thiol compound (A), and 1.41 g of C6DA was added to 0.47 g of a mixture obtained by mixing EGMP and TPP at EGMP/TPP (mass ratio)=20/0.1. Then, 4.89 g of PEMP was added thereto and the mixture was stirred at room temperature (25° C.) to obtain a composition (E-13). The amount of TPP with respect to a total amount of EGMP and PEMP is 0.044% by mass.

Comparative Example 2-1

A composition (E-14) was obtained by performing a reaction in the same manner as in Example 1, except that 1.13 g of C6DA was added to 3.18 g of a mixture of PEMP and TPP.

Comparative Example 2-2

A composition (E-15) was obtained by performing a reaction in the same manner as in Example 1, except that 1.81 g of C6DA was added to 3.91 g of a mixture of PEMP and TPP.

Comparative Example 2-3

59.2 g of TMPTA, 600 g of methyl ethyl ketone (MEK, boiling point 79° C.) and 259.2 g of PEMA were added into a 2 L four-necked flask equipped with a stirrer, a nitrogen inlet pipe, a thermometer, and a condenser, and the reaction mixture was heated to a reflux temperature with stirring under a nitrogen atmosphere. After stirring for 2 hours, the mixture was cooled to finish a Michael addition reaction, thereby obtaining a composition (E-16).

Comparative Example 2-4

A composition (E-17) was obtained by performing a Michael addition reaction in the same manner as in Comparative Example 3, except that 432 g of PEMA, 400 g of MEK, and 296 g of TMPTA were added to the reaction vessel to prepare a reaction mixture.

Reference Example 2-1

A polyfunctional compound (E-18) was obtained by performing a reaction in the same manner as in Example 1, except that EGMP was used instead of PEMP as the polyfunctional thiol compound (A), and 2.26 g of C6DA was added to 5.58 g of a mixture obtained by mixing EGMP and TPP at EGMP/TPP (mass ratio)=10/0.1.

In the compositions (E-1) to (E-18) obtained in the respective Examples, x', y', and r' based on the charged amounts can be used as they are for x, y, and r.

r is ($f_B$×molar equivalent of compound (B))/($f_A$×molar equivalent of polyfunctional thiol compound (A)), and represents a molar ratio (reactive groups/thiol groups) during the reaction.

The amounts of the compounds (A) to (C), the amount of solvent, the reaction temperature (external temperature), the values of $f_A$, $f_B$, $f_A+f_B$, r, and r×($f_A-1$)×($f_B-1$), and the evaluation results of the solubility in MMA in each of Examples are shown in Table 2 or 3.

The solubility in MMA was evaluated as follows. The composition was added and mixed so that the concentration was 1% by mass with respect to methyl methacrylate (MMA) at room temperature (25° C.), the dissolution state was visually confirmed, and the solubility was evaluated according to the following criteria.

A (Favorable): The composition was dissolved making the solution uniform.

D (Poor): The composition was not dissolved making the solution non-uniform.

TABLE 2

| | | Number of functional groups | Example | | | | | | | | |
|---|---|---|---|---|---|---|---|---|---|---|---|
| | | | 2-1 | 2-2 | 2-3 | 2-4 | 2-5 | 2-6 | 2-7 | 2-8 | 2-9 |
| Polyfunctional thiol compound (A) [molar equivalent] | EGMP | 2 | — | — | — | — | — | — | — | — | — |
| | PEMA | 4 | — | — | — | — | — | — | — | — | — |
| | PEMP | 4 | 1.5 | 2.0 | 2.5 | 3.0 | 4.0 | — | — | 2.0 | 2.0 |
| | DPMP | 6 | — | — | — | — | — | 2.0 | 2.3 | — | — |
| | $f_A$ | | 4.0 | 4.0 | 4.0 | 4.0 | 4.0 | 6.0 | 6.0 | 4.0 | 4.0 |
| Compound (B) [molar equivalent] | EHA | 1 | — | — | — | — | — | — | — | 1.0 | 1.0 |
| | C6DA | 2 | 1.0 | 1.0 | 1.0 | 1.0 | 1.0 | 1.0 | 1.0 | — | — |
| | TMPTA | 3 | — | — | — | — | — | — | — | — | — |
| | NPGE | 2 | — | — | — | — | — | — | — | 1.0 | — |
| | TMHMDI | 2 | — | — | — | — | — | — | — | — | 1.0 |
| | $f_B$ | | 2.0 | 2.0 | 2.0 | 2.0 | 2.0 | 2.0 | 2.0 | 1.5 | 1.5 |
| Catalyst (C) [% by mass] | TPP | | 1.0 | 1.0 | 1.0 | 1.0 | 1.0 | 1.0 | 1.0 | — | — |
| | CHDP | | — | — | — | — | — | — | — | 0.5 | 0.5 |
| Solvent [gram equivalent] | MEK | | — | — | — | — | — | — | — | — | — |
| Reaction temperature [° C.] | | | 50 | 50 | 50 | 50 | 50 | 50 | 50 | 50 | 50 |
| Composition | | | (E-1) | (E-2) | (E-3) | (E-4) | (E-5) | (E-6) | (E-7) | (E-8) | (E-9) |
| $f_A + f_B$ | | | 6.0 | 6.0 | 6.0 | 6.0 | 6.0 | 8.0 | 8.0 | 5.5 | 5.5 |
| r | | | 1/3 | 1/4 | 1/5 | 1/6 | 1/8 | 1/6 | 1/6.8 | 1/2.67 | 1/2.67 |
| r($f_A - 1$)($f_B - 1$) | | | 1.0 | 0.75 | 0.6 | 0.5 | 0.38 | 0.83 | 0.73 | 0.56 | 0.56 |
| Solubility in MMA | | | A | A | A | A | A | A | A | A | A |

TABLE 3

| | | Number of functional groups | Example | | | | Comparative Example | | | | Reference Example |
|---|---|---|---|---|---|---|---|---|---|---|---|
| | | | 2-10 | 2-11 | 2-12 | 2-13 | 2-1 | 2-2 | 2-3 | 2-4 | 2-1 |
| Polyfunctional thiol compound (A) [molar equivalent] | EGMP | 2 | — | — | — | 1.0 | — | — | — | — | 1.5 |
| | PEMA | 4 | — | — | — | — | — | — | 3.0 | 1.0 | — |
| | PEMP | 4 | 2.0 | 1.5 | 1.5 | 8.0 | 1.3 | 1.0 | — | — | — |
| | DPMP | 6 | — | — | — | — | — | — | — | — | — |
| | $f_A$ | | 4.0 | 4.0 | 4.0 | 3.8 | 4.0 | 4.0 | 4.0 | 4.0 | 2.0 |
| Compound (B) [molar equivalent] | EHA | 1 | 1.0 | 1.0 | 0.5 | — | — | — | — | — | — |
| | C6DA | 2 | 1.0 | 1.0 | 1.0 | 5.0 | 1.0 | 1.0 | — | — | 1.0 |
| | TMPTA | 3 | — | — | — | — | — | — | 1.0 | 1.0 | — |
| | NPGE | 2 | — | — | — | — | — | — | — | — | — |
| | TMHMDI | 2 | — | — | — | — | — | — | — | — | — |
| | $f_B$ | | 1.5 | 1.5 | 1.67 | 2.0 | 2.0 | 2.0 | 3.0 | 3.0 | 2.0 |
| Catalyst (C) [% by mass] | TPP | | — | — | — | 0.044 | 1.0 | 1.0 | — | — | 1.0 |
| | CHDP | | 0.5 | 0.5 | 0.5 | — | — | — | — | — | — |
| Solvent [gram equivalent] | MEK | | — | — | — | — | — | — | 10 | 10 | — |
| Reaction temperature [° C.] | | | 50 | 50 | 50 | 50 | 50 | 50 | 100 | 100 | 50 |
| Composition | | | (E-10) | (E-11) | (E-12) | (E-13) | (E-14) | (E-15) | (E-16) | (E-17) | (E-18) |
| $f_A + f_B$ | | | 5.5 | 5.5 | 5.67 | 5.8 | 6.0 | 6.0 | 7.0 | 7.0 | 4.0 |
| r | | | 1/2.67 | 1/2 | 1/2.4 | 1/3.42 | 1/2.5 | 1/2 | 1/4 | 1/1.33 | 1/1.5 |
| $r(f_A - 1)(f_B - 1)$ | | | 0.56 | 0.75 | 0.83 | 0.82 | 1.2 | 1.5 | 1.5 | 4.5 | 0.67 |
| Solubility in MMA | | | A | A | A | A | D | D | D | D | A |

As shown in Tables 2 and 3, the compositions (E-1) to (E-13) of Examples 2-1 to 2-13 and the composition (E-18) of Reference Example 2-1 had excellent solubility in MMA. On the other hand, the compositions (E-14) to (E-17) of Comparative Examples 2-1 to 2-4 had poor solubility in MMA.

From the above, it was confirmed that the composition according to the present invention exhibits excellent characteristics.

Examples 2-14 to 2-17

A chain transfer agent, MMA, as a radically polymerizable monomer (D), azobisbutyronitrile (AIBN) as a polymerization initiator, and toluene as a solvent were added into a 250 mL four-necked separable flask equipped with a stirrer, a nitrogen inlet pipe, a thermometer, and a condenser, toluene as a solvent were added thereto and mixed at the composition shown in Table 4, and the reaction mixture was heated to 80° C. with stirring under a nitrogen atmosphere. After heating and stirring for 5 hours, the mixture was reprecipitated using hexane as a poor solvent to obtain a branched polymer.

Comparative Examples 2-5 to 2-8

A polymer was produced in the same manner as in Example 2-14, except that the composition of the reaction mixture was changed as shown in Table 4.

The measurement results of the relative Mw of the polymer and the solution viscosity of the polymer in Examples 2-14 to 2-17 and Comparative Examples 2-5 to 2-8 are shown in Table 4.

The solution viscosity of the polymer was measured as follows. The polymer was dissolved in butyl acetate, the solid content concentration was adjusted to 40% by mass, and the solution viscosity was measured at room temperature (25° C.), using an E-type viscometer.

TABLE 4

| | | Example | | | | Comparative Example | | | |
|---|---|---|---|---|---|---|---|---|---|
| | | 2-14 | 2-15 | 2-16 | 2-17 | 2-5 | 2-6 | 2-7 | 2-8 |
| Monomer [% by mole] | MMA | 100 | 100 | 100 | 100 | 100 | 100 | 100 | 100 |
| Polymerization initiator [% by mole] | AIBN | 0.3 | 0.3 | 0.3 | 0.3 | 0.3 | 0.3 | 0.3 | 0.3 |
| Solvent [gram equivalent] | Toluene | 1.0 | 1.0 | 1.0 | 1.0 | 1.0 | 1.0 | 1.0 | 1.0 |
| Chain transfer agent [% by mass] | E-1 | 13 | — | — | — | — | — | — | — |
| | E-3 | — | 6 | — | — | — | — | — | — |
| | E-6 | — | — | 9 | — | — | — | — | — |
| | E-13 | — | — | — | 14 | — | — | — | — |
| | PEMP | — | — | — | — | — | 4 | — | — |
| | DPMP | — | — | — | — | — | — | 4 | — |
| | E-18 | — | — | — | — | — | — | — | 4 |

TABLE 4-continued

| | Example | | | | Comparative Example | | | |
|---|---|---|---|---|---|---|---|---|
| | 2-14 | 2-15 | 2-16 | 2-17 | 2-5 | 2-6 | 2-7 | 2-8 |
| Polymerization temperature [° C.] | 80 | 80 | 80 | 80 | 80 | 80 | 80 | 80 |
| Polymerization time [hours] | 5 | 5 | 5 | 5 | 5 | 5 | 5 | 5 |
| Weight-average molecular weight (Mw) | 29,900 | 20,000 | 31,500 | 24,000 | 34,500 | 16,400 | 24,700 | 18,900 |
| Polymer solution viscosity [mPa · s] | 520 | 1,570 | 2,520 | 900 | 156,100 | 3,950 | 4,170 | 45,000 |

As shown in Table 4, in Examples 2-14 to 2-17 in which the compositions (E-1), (E-3), (E-6), and (E-13) were used as the chain transfer agent, the viscosity of the polymer solution was low and the handleability was excellent even when the branched polymer had a high molecular weight. On the other hand, in Comparative Example 2-5 in which a chain transfer agent was not used, and Comparative Examples 2-6 and 2-7 in which a chain transfer agent with less branches was used, the viscosity of the polymer solution was high even though the polymer had the same degree of molecular weight as those in Examples 2-14 to 2-17. In addition, in Comparative Example 2-8 in which the composition (E-18) was used as the chain transfer agent, the number of polymer branches was insufficient, and the viscosity of the polymer solution was thus high.

Production Example 3-1

To 10 g of PEMP, as a polyfunctional thiol compound (A), 0.1 g of finely crushed TPP as a catalyst (C) was added, and the mixture was heated to 80° C. with stirring until the mixture was uniform, thereby completely dissolving the components. To 7.33 g of the obtained mixture, 2.26 g of C6DA as a compound (B) was added, and the mixture was stirred at room temperature (25° C.) at a molar ratio of PEMP to C6DA of 1.5:1.0 to obtain a thiol group-containing compound (G-1).

Production Example 3-2

A compound (X-1) having a thioether structure but not having a thiol group was produced in the same manner as in Production Example 3-1, except that 3.6 parts by mass of stearyl-3-mercaptopropionate (STMP, manufactured by SC Organic Chemical Co., Ltd.) was used instead of PEMP.

Example 3-1

The thiol group-containing compound (G-1) and VHK, as a thermoplastic resin (H), were mixed such that the mass ratio (G/H) was 1/99, and stirred at room temperature (25° C.) to prepare a resin composition.

Comparative Examples 3-1 and 3-2

A resin composition was prepared in the same manner as in Example 3-1, except that the composition was changed as shown in Table 5.
Furthermore, in Comparative Example 3-2, PMMA-SH was used as the compound (X-2) having a thiol group but not having a thioether structure and a thiourethane structure.
The relative Mw of a thiol group-containing compound (G) and a comparative compound (X) used in Examples and Comparative Examples, the resin composition, and the evaluation results are shown in Table 5.

TABLE 5

| | | Example | Comparative Example | |
|---|---|---|---|---|
| | | 3-1 | 3-1 | 3-2 |
| Thiol group-containing compound (G) | Type | G-1 | — | — |
| | Mw | 10,700 | — | — |
| Comparative compound (X) | Type | — | X-1 | X-2 |
| | Mw | — | 21,000 | 15,000 |
| Thermoplastic resin (H) | | VHK | VH | VH |
| Mass ratio (G/H) | | 1/99 | 10/90 | 10/90 |
| 5% weight reduction temperature (Td5) [° C.] | G (measured value) | 346.0 | 340.3 | 317.3 |
| | H (measured value) | 319.0 | 338.8 | 338.8 |
| | G + H (measured value) | 344.3 | 336.1 | 316.5 |
| | G + H (calculated value) | 319.3 | 338.9 | 338.3 |
| | Δ(G + H) | 25.0 | −2.8 | −21.8 |

The "G (measured value)" column of the 5%-by-weight reduction temperature (Td5) in Table 5 shows measured values of Td5 of the thiol group-containing compound (G) or the comparative compound (X).
The "H (measured value)" column shows measured values of Td5 of the thermoplastic resin (H) or the comparative compound (X).
The "G+H (measured value)" column shows measured values of Td5 of the resin composition.
The "G+H (calculated value)" column shows values of Td5 calculated from a mass ratio of the thermogravimetric measurement value of the thiol group-containing compound (G) or the comparative compound and the thermogravimetric measurement value of the thermoplastic resin (H).
"Δ(G+H)" is a difference between "G+H (measured value)" and "G+H (calculated value)", and is ΔTd5.
As shown in Table 5, it was found that the resin composition of each of Comparative Examples 3-1 and 3-2 not including the thiol group-containing compound (G) has ΔTd5 (Δ(G+H)) of 0 or less, whereas the resin composition of Example 3-1 including the thiol group-containing compound (G) and the thermoplastic resin (H) has a ΔTd5 of more than 0 and has an effect of improving the heat resistance. In addition, in Example 3-1, no odor was generated during heating at the time of measuring the 5%-by-weight reduction temperature.

Production Example 4-1

To 10 g of PEMP, as a polyfunctional thiol compound (A), 0.05 g of finely crushed TPP as a catalyst (C) was added, and the mixture was heated to 80° C. with stirring until the mixture was uniform, thereby completely dissolving the components. To 7.33 g of the obtained mixture, 2.26 g of C6DA as a compound (B) and 0.92 g of EHA were added, and the mixture was stirred at room temperature (25° C.) and stirred at 50° C. for 3 hours at a molar ratio of PEMP to C6DA to EHA of 1.5:1.0:0.5 to obtain a chain transfer agent (F-11). The relative Mw was 16,000.

Production Example 4-2

A chain transfer agent (F-12) was obtained in the same manner as in Production Example 4-1, except that A-DOD-N was used instead of C6DA and the molar ratio of PEMP to A-DOD-N was 1.5:1.0. The relative Mw was 23,000.

Production Example 4-3

A chain transfer agent (F-13) was obtained in the same manner as in Production Example 4-1, except that A-DCP was used instead of C6DA and the molar ratio of PEMP to A-DCP was 2.0:1.0. The relative Mw was 8,000.

Production Example 4-4

A chain transfer agent (F-14) was obtained in the same manner as in Production Example 4-1, except that A-DOD-N was used instead of C6DA, LA was used instead of EHA, and the molar ratio of PEMP to A-DOD-N to LA was 1.5:1.0:0.5. The relative Mw was 13,000.

Example 4-1

50% by mole of LMA and 50% by mole of BMA as a radically polymerizable monomer (D), the chain transfer agent (F-11) obtained in Production Example 4-1 in the amount of 7.1 parts by mass with respect to 100 parts by mass of a total amount of radically polymerizable monomers (D), and 0.25 parts by mass of 2,2'-azobisbutyronitrile (AIBN) as a polymerization initiator were added into a 500 mL separable flask equipped with a stirrer, a thermometer, a nitrogen inlet pipe, and a condenser, 300 parts by mass of toluene as a solvent was further added thereto, and the reaction mixture was heated to 80° C. with stirring under a nitrogen atmosphere. After heating and stirring for 5 hours, the mixture was reprecipitated using methanol as a poor solvent and dried to obtain a high-molecular-weight compound.

Example 4-2

A high-molecular-weight compound was obtained in the same manner as in Example 4-1, except that 50% by mole of TDMA and 50% by mole of BMA as the radically polymerizable monomers (D), and 6.8 parts by mass of (F-11) were used as the chain transfer agent (F).

Example 4-3

A high-molecular-weight compound was obtained in the same manner as in Example 4-1, except that 6.8 parts by mass of the chain transfer agent (F-12) was used as the chain transfer agent (F).

Example 4-4

A high-molecular-weight compound was obtained in the same manner as in Example 4-1, except that 35% by mole of LMA and 65% by mole of BMA were used as the radically polymerizable monomer (D) and 6.9 parts by mass of (F-12) was used as the chain transfer agent (F).

Example 4-5

A high-molecular-weight compound was obtained in the same manner as in Example 4-1, except that 100% by mole of EHMA was used as the radically polymerizable monomer (D) and 6.5 parts by mass of (F-13) was used as the chain transfer agent (F).

Example 4-6

A high-molecular-weight compound was obtained in the same manner as in Example 4-1, except that 35% by mole of LMA and 65% by mole of BMA were used as the radically polymerizable monomer (D) and 8.3 parts by mass of (F-14) was used as the chain transfer agent (F).

Example 4-7

A high-molecular-weight compound was obtained in the same manner as in Example 4-1, except that 50% by mole of and 50% by mole of MMA were used as the radically polymerizable monomer (D) and 8.5 parts by mass of (F-14) was used as the chain transfer agent (F).

Comparative Example 4-1

A high-molecular-weight compound was obtained in the same manner as in Example 4-1, except that 100% by mole of EHMA was used as the radically polymerizable monomer (D) and 2.0 parts by mass of PEMP was used as the chain transfer agent.

The results of the relative Mw and the absolute Mw/relative Mw of the high-molecular-weight compounds obtained in Examples and Comparative Examples, and the kinematic viscosity (mm$^2$/s), the viscosity index (VI), and the shear stability index (SSI) of the 10% YUBASE2 solution are shown in Table 6.

Furthermore, the viscosity index (VI) is a physical property value that indicates the temperature dependence of the viscosity of the lubricating oil, and the larger the value, the smaller the viscosity change due to the temperature. The shear stability index (SSI) is an index that indicates how much an increase in the viscosity of the lubricating oil due to the addition of the high-molecular-weight compound (additive for a lubricating oil) is reduced by a shearing force, and the value which is closer to 0 is more preferable.

TABLE 6

|  |  | Example | | | | | | | Comparative Example |
|---|---|---|---|---|---|---|---|---|---|
|  |  | 4-1 | 4-2 | 4-3 | 4-4 | 4-5 | 4-6 | 4-7 | 4-1 |
| Radically polymerizable monomer (D) [% by mole] | EHMA | — | — | — | — | 100 | — | — | 100 |
| | LMA | 50 | — | 50 | 35 | — | 35 | 50 | — |
| | TDMA | — | 50 | — | — | — | — | — | — |
| | BMA | 50 | 50 | 50 | 65 | — | 65 | — | — |
| | MMA | — | — | — | — | — | — | 50 | — |
| Chain transfer agent (F) [parts by mass] | F-11 | 7.1 | 6.8 | — | — | — | — | — | — |
| | F-12 | — | — | 6.8 | 6.9 | — | — | — | — |
| | F-13 | — | — | — | — | 6.5 | — | — | — |
| | F-14 | — | — | — | — | — | 8.3 | 8.5 | — |
| | PEMP | — | — | — | — | — | — | — | 2.0 |
| Relative Mw | | 34,000 | 30,000 | 36,000 | 37,000 | 22,000 | 40,000 | 31,000 | 23,000 |
| Absolute Mw/relative Mw | | 1.30 | 1.31 | 1.38 | 1.38 | 1.78 | 1.35 | 1.43 | 1.20 |
| Kinematic viscosity and viscosity index | Before KRL 20 h | Vk40 | 16.66 | 16.08 | 16.70 | 16.27 | 16.19 | 16.15 | 15.24 | 16.37 |
| | | Vk100 | 4.409 | 4.225 | 4.411 | 4.280 | 4.111 | 4.317 | 4.052 | 4.228 |
| | | Viscosity index (VI) | 191 | 181 | 190 | 184 | 165 | 191 | 179 | 175 |
| | After KRL 20 h | Vk40 | 16.28 | 15.81 | 16.41 | 16.23 | 16.00 | 15.99 | 15.15 | 16.10 |
| | | Vk100 | 4.298 | 4.129 | 4.309 | 4.266 | 4.048 | 4.225 | 4.032 | 4.115 |
| | | Viscosity index (VI) | 186 | 175 | 184 | 178 | 161 | 183 | 178 | 167 |
| Shear stability index (SSI) | | 6.1 | 5.9 | 5.6 | 3.2 | 4.2 | 5.4 | 1.4 | 6.9 |

As described above, an effect of improving the viscosity index and the shear stability are easily traded off, but as shown in Table 6, the high-molecular-weight compounds of Examples 4-1 to 4-7 according to the present invention had a sufficient viscosity index (VI) and a small SSI, and the lubricating oils to which the high-molecular-weight compounds had been added also had excellent shear stability. In particular, the high-molecular-weight compounds of Examples 4-1 to 4-4 and 4-6 to 4-7 achieved both a high VI value of about 180 or more and favorable shear stability. On the other hand, in Comparative Example 4-1, the viscosity index (VI) was sufficient but since the SSI was large, the lubricating oil to which the high-molecular-weight compound was added had insufficient shear stability.

This supports the fact that the high-molecular-weight compound of the present invention achieves both of an effect of improving viscosity index, and high shear stability.

What is claimed is:

1. A high-molecular-weight compound comprising a plurality of polymer chains linked through a divalent or higher-valent linking group and having a moiety derived from a polyfunctional thiol compound (A) and a moiety derived from a compound (B) having a reactive group that reacts with a thiol group,
   wherein the divalent or higher-valent linking group has a thiol group and at least one of a thioether structure and a thiourethane structure,
   a ratio of an absolute weight-average molecular weight to a relative weight-average molecular weight (absolute Mw/relative Mw) of the high-molecular-weight compound is 1.25 or more, and
   a relative Mw of the high-molecular-weight compound is 15,000 or more and 350,000 or less,
   the high-molecular-weight compound satisfies Formulae (11) and (12), $$r \times (f_A - 1) \times (f_B - 1) < 1.2 \quad (11)$$

$$r = (f_B \times y)/(f_A \times x) \quad (12)$$

wherein, in Formula (11), $f_A$ is an average number of thiol groups per molecule of the polyfunctional thiol compound (A), $f_B$ is an average number of reactive groups per molecule of the compound (B), $f_A$ is 2.0 or more and $f_B$ is 1.2 or more, provided that a case where only the compound (A) having two thiol groups and only the compound (B) having two reactive groups are used is excluded, and r is a value calculated by Formula (12) when a molar ratio of the moiety derived from the polyfunctional thiol compound (A) to the moiety derived from the compound (B) is defined as x:y.

2. The high-molecular-weight compound according to claim 1, wherein the divalent or higher-valent linking group includes at least one of structures represented by Formulae (1) and (2),

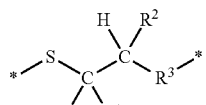
(1)

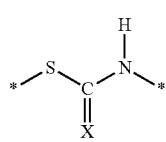
(2)

wherein, in Formula (1), $R^1$ and $R^2$ are each independently a hydrogen atom, a monovalent hydrocarbon group, a hydroxyl group, or a monovalent electron-withdrawing group, and $R^3$ is an oxygen atom, a divalent hydrocarbon group, or a divalent electron-withdrawing group, in Formula (2), X is an oxygen atom or a sulfur atom, and in Formulae (1) and (2), -* is a bond.

3. The high-molecular-weight compound according to claim 1, wherein the divalent or higher-valent linking group has 1 to 300 thiol groups per molecule of the high-molecular-weight compound.

4. The high-molecular-weight compound according to claim 1, wherein the absolute Mw/relative Mw is 3.00 or less.

5. A method for producing the high-molecular-weight compound of claim 1, comprising:
   a step of reacting the polyfunctional thiol compound (A) with the compound (B) having a reactive group that reacts with a thiol group to obtain a chain transfer agent (F) having a thiol group; and
   a step of polymerizing vinyl-based compounds in the presence of the chain transfer agent (F) having a thiol group and a radical polymerization initiator to obtain a high-molecular-weight compound,
   wherein the method comprises a step of reacting the polyfunctional thiol compound (A) and the compound (B) having a reactive group that reacts with a thiol group under conditions satisfying Formulae (13) and (14), $$r' \times (f_A-1) \times (f_B-1) < 1.2 \quad (13)$$

$$r' = (f_B \times y')/(f_A \times x') \quad (14)$$

wherein, in Formula (13), $f_A$ is an average number of thiol groups per molecule of the polyfunctional thiol compound (A), $f_B$ is an average number of reactive groups per molecule of the compound (B), $f_A$ is 2.0 or more and $f_B$ is 1.2 or more, provided that a case where only the compound (A) having two thiol groups and only the compound (B) having two reactive groups are used is excluded, and r' is a value calculated by Formula (14) when a molar ratio of the polyfunctional thiol compound (A) to the compound (B) is x':y'.

6. The method for producing a high-molecular-weight compound according to claim 5, wherein the reactive group that reacts with a thiol group is one or more selected from the group consisting of an acrylate group, a glycidyl group, and an isocyanate group.

7. The high-molecular-weight compound according to claim 1, wherein the composition satisfies $f_A+f_B>4.0$.

8. The high-molecular-weight compound according to claim 1, wherein the reactive group that reacts with a thiol group is one or more selected from the group consisting of an acrylate group, a glycidyl group, and an isocyanate group.

9. The high-molecular-weight compound according to claim 1, wherein the composition is a chain transfer agent in a radical polymerization reaction system.

10. The method for producing the high-molecular-weight compound according to claim 5, wherein the composition satisfies $f_A+f_B>4.0$.

11. The method for producing the high-molecular-weight compound according to claim 5, wherein the polyfunctional thiol compound (A) is reacted with the compound (B) having a reactive group that reacts with a thiol group in the presence of a catalyst (C).

12. The method for producing the high-molecular-weight compound according to claim 5,
   wherein the amount of solvent at a starting time of the reaction between the polyfunctional thiol compound (A) and the compound (B) having a reactive group that reacts with a thiol group is 50% by mass or less of a total mass of the polyfunctional thiol compound (A) and the compound (B) having a reactive group that reacts with a thiol group, and
   an external temperature during the reaction between the polyfunctional thiol compound (A) and the compound (B) having a reactive group that reacts with a thiol group is 10° C. to 50° C.

13. A resin composition comprising:
   the high-molecular-weight compound according to claim 1; and
   a thermoplastic resin.

14. The resin composition according to claim 13, wherein a mass ratio of the high-molecular-weight compound or the composition to the thermoplastic resin ((high-molecular-weight compound or composition)/thermoplastic resin) is 0.1/99.9 to 95/5.

15. An additive for a lubricating oil, wherein the additive for a lubricating oil comprises a high-molecular-weight compound,
   the high-molecular-weight compound comprising:
   a plurality of polymer chains linked through a divalent or higher-valent linking group and having a moiety derived from a polyfunctional thiol compound (A) and a moiety derived from a compound (B) having a reactive group that reacts with a thiol group,
   wherein the divalent or higher-valent linking group has a thiol group and at least one of a thioether structure and a thiourethane structure,
   a ratio of an absolute weight-average molecular weight to a relative weight-average molecular weight (absolute Mw/relative Mw) of the high-molecular-weight compound is 1.25 or more, and
   a relative Mw of the high-molecular-weight compound is 15,000 or more and 45,000 or less,
   the high-molecular-weight compound satisfies Formulae (11) and (12), $$r \times (f_A-1) \times (f_B-1) < 1.2 \quad (11)$$

$$r = (f_B \times y)/(f_A \times x) \quad (12)$$

wherein, in Formula (11), $f_A$ is an average number of thiol groups per molecule of the polyfunctional thiol compound (A), $f_B$ is an average number of reactive groups per molecule of the compound (B), $f_A$ is 2.0 or more and $f_B$ is 1.2 or more, provided that a case where only the compound (A) having two thiol groups and only the compound (B) having two reactive groups are used is excluded, and r is a value calculated by Formula (12) when a molar ratio of the moiety derived from the polyfunctional thiol compound (A) to the moiety derived from the compound (B) is defined as x:y.

16. A lubricating oil comprising the additive for a lubricating oil,
   wherein the lubricating oil comprises a high-molecular-weight compound comprising a plurality of polymer chains linked through a divalent or higher-valent linking group,
   the divalent or higher-valent linking group has a thiol group and at least one of a thioether structure and a thiourethane structure, and
   a ratio of an absolute weight-average molecular weight to a relative weight-average molecular weight (absolute Mw/relative Mw) of the high-molecular-weight compound is 1.25 or more.

17. A high-molecular-weight compound comprising a plurality of polymer chains linked through a divalent or higher-valent linking group and having a moiety derived from a polyfunctional thiol compound (A) and a moiety derived from a compound (B) having a reactive group that reacts with a thiol group,
   wherein the divalent or higher-valent linking group has a thiol group and at least one of a thioether structure and a thiourethane structure, a ratio of an absolute weight-average molecular weight to a relative weight-average molecular weight (absolute Mw/relative Mw) of the high-molecular-weight compound is 1.25 or more and 2.10 or less, and a relative Mw of the high-molecular-weight compound is 15,000 or more and 350,000 or less, the high-molecular-weight compound satisfies Formulae (11) and (12), $$r \times (f_A-1) \times (f_B-1) < 1.2 \quad (11)$$

$$r = (f_B \times y)/(f_A \times x) \quad (12)$$

wherein, in Formula (11), $f_A$ is an average number of thiol groups per molecule of the polyfunctional thiol compound (A), $f_B$ is an average number of reactive groups per molecule of the compound (B), $f_A$ is 2.0 or more and $f_B$ is 1.2 or more, provided that a case where only the compound (A) having two thiol groups and only the compound (B) having two reactive groups are used is excluded, and r is a value calculated by Formula (12) when a molar ratio of the moiety derived from the polyfunctional thiol compound (A) to the moiety derived from the compound (B) is defined as x:y.

18. A high-molecular-weight compound comprising a plurality of polymer chains linked through a divalent or higher-valent linking group and having a moiety derived from a polyfunctional thiol compound (A) and a moiety derived from a compound (B) having a reactive group that reacts with a thiol group, wherein the divalent or higher-valent linking group has a thiol group and at least one of a thioether structure and a thiourethane structure, a ratio of an absolute weight-average molecular weight to a relative weight-average molecular weight (absolute Mw/relative Mw) of the high-molecular-weight compound is 1.25 or more and 2.00 or less, and a relative Mw of the high-molecular-weight compound is 15,000 or more and 350,000 or less, the high-molecular-weight compound satisfies Formulae (11) and (12), $$r \times (f_A-1) \times (f_B-1) < 1.2 \quad (11)$$

$$r = (f_B \times y)/(f_A \times x) \quad (12)$$

wherein, in Formula (11), $f_A$ is an average number of thiol groups per molecule of the polyfunctional thiol compound (A), $f_B$ is an average number of reactive groups per molecule of the compound (B), $f_A$ is 2.0 or more and $f_B$ is 1.2 or more, provided that a case where only the compound (A) having two thiol groups and only the compound (B) having two reactive groups are used is excluded, and r is a value calculated by Formula (12) when a molar ratio of the moiety derived from the polyfunctional thiol compound (A) to the moiety derived from the compound (B) is defined as x:y.

19. A high-molecular-weight compound comprising a plurality of polymer chains linked through a divalent or higher-valent linking group and having a moiety derived from a polyfunctional thiol compound (A) and a moiety derived from a compound (B) having a reactive group that reacts with a thiol group, wherein the divalent or higher-valent linking group has a thiol group and at least one of a thioether structure and a thiourethane structure, a ratio of an absolute weight-average molecular weight to a relative weight-average molecular weight (absolute Mw/relative Mw) of the high-molecular-weight compound is 1.25 or more and 1.95 or less, and a relative Mw of the high-molecular-weight compound is 15,000 or more and 350,000 or less, the high-molecular-weight compound satisfies Formulae (11) and (12), $$r \times (f_A-1) \times (f_B-1) < 1.2 \quad (11)$$

$$r = (f_B \times y)/(f_A \times x) \quad (12)$$

wherein, in Formula (11), $f_A$ is an average number of thiol groups per molecule of the polyfunctional thiol compound (A), $f_B$ is an average number of reactive groups per molecule of the compound (B), $f_A$ is 2.0 or more and $f_B$ is 1.2 or more, provided that a case where only the compound (A) having two thiol groups and only the compound (B) having two reactive groups are used is excluded, and r is a value calculated by Formula (12) when a molar ratio of the moiety derived from the polyfunctional thiol compound (A) to the moiety derived from the compound (B) is defined as x:y.

* * * * *